US012642546B2

(12) United States Patent　　　(10) Patent No.:　US 12,642,546 B2
　　Behan et al.　　　　　　　　　　(45) Date of Patent:　　　Jun. 2, 2026

(54) CATHETER SYSTEM WITH HIGHLY FLEXIBLE DISTAL PORTION FOR DISTAL ACCESS AND/OR CLOT REMOVAL

(71) Applicant: Julier Medical SAS, Paris (FR)

(72) Inventors: Niall Behan, Dubendorf (CH); Marcus Wenzel, Grossenhain (DE)

(73) Assignee: Julier Medical SAS, Paris (FR)

( * ) Notice: Subject to any disclaimer, the term of this patent is extended or adjusted under 35 U.S.C. 154(b) by 0 days.

(21) Appl. No.: 19/279,781

(22) Filed: Jul. 24, 2025

(65) Prior Publication Data

US 2026/0026825 A1　　Jan. 29, 2026

(30) Foreign Application Priority Data

Jul. 26, 2024　(EP) ..................................... 24306270

(51) Int. Cl.
　A61B 17/22　　　(2006.01)
　A61M 25/00　　　(2006.01)
　A61M 25/01　　　(2006.01)
(52) U.S. Cl.
　CPC ..... A61B 17/22031 (2013.01); A61M 25/005 (2013.01); A61M 25/0074 (2013.01);
　　　　　　　(Continued)
(58) Field of Classification Search
　CPC .... A61B 17/22031; A61B 2017/22035; A61B 2017/22072; A61B 2017/22074;
　　　　　　　(Continued)

(56) References Cited

U.S. PATENT DOCUMENTS 3,868,956 A　　3/1975　Alfidi et al.
3,946,741 A　　3/1976　Adair
　　　　　　(Continued)

FOREIGN PATENT DOCUMENTS

DE　　102011100733 A1　11/2012
EP　　　　0379794 A1　　8/1990
　　　　　　(Continued)

OTHER PUBLICATIONS

Alawieh, et al., Impact of Procedure Time on Outcomes of Thrombectomy for Stroke, JACC, 73(8):779-890 (Mar. 2019).
　　　　　　(Continued)

*Primary Examiner* — Robert A Lynch
(74) *Attorney, Agent, or Firm* — Greenberg Traurig, LLP; Christopher C. Bolten; Robert D. Ward

(57)　　　　　　ABSTRACT
An improved catheter is provided for accessing a site in a patient's vasculature, delivery a device or instrument to the site, removing an obstruction(s) from a blood vessel, and/or for retrieving a clot/thrombus in the neurovasculature for the treatment of stroke. The catheter has a collapsed state sufficiently small and flexible for easier delivery through challenging vasculature and also has an expanded state sufficiently sized and robust for removing the obstruction. The catheter may include a self-collapsing and expanding mechanism to transition a portion of an outer tube (e.g., a braided portion) between the collapsed and expanded states. Such mechanism may include an inner actuator tube slidable over an actuation wire to collapse a plurality of struts engaged with the actuation wire, thereby collapsing the braided portion. The catheter may also include an intermediate coiled tube for reinforcing the braided portion in the expanded state.

30 Claims, 22 Drawing Sheets

(52) U.S. Cl.
CPC .... *A61M 25/0108* (2013.01); *A61M 25/0136*
(2013.01); *A61B 2017/22079* (2013.01)

(58) Field of Classification Search
CPC ...... A61B 2017/22079; A61M 25/005; A61M
25/0067; A61M 25/0068; A61M 25/0069;
A61M 25/0074; A61M 25/0102; A61M
25/0108; A61M 25/0136
See application file for complete search history.

(56) References Cited

U.S. PATENT DOCUMENTS

| | | | |
|---|---|---|---|
| 4,228,802 A | 10/1980 | Trott | |
| 4,329,995 A | 5/1982 | Anthracite | |
| 4,762,125 A | 8/1988 | Leiman et al. | |
| 4,873,978 A | 10/1989 | Ginsburg | |
| 4,926,858 A | 5/1990 | Gifford, III et al. | |
| 5,011,488 A | 4/1991 | Ginsburg | |
| 5,030,201 A | 7/1991 | Palestrant | |
| 5,092,839 A | 3/1992 | Kipperman | |
| 5,102,415 A | 4/1992 | Guenther et al. | |
| 5,234,425 A | 8/1993 | Fogarty et al. | |
| 5,256,146 A | 10/1993 | Ensminger et al. | |
| 5,318,532 A | 6/1994 | Frassica | |
| 5,458,573 A | 10/1995 | Summers | |
| 5,695,499 A | 12/1997 | Helgerson et al. | |
| 5,776,096 A | 7/1998 | Fields | |
| 5,807,311 A | 9/1998 | Palestrant | |
| 5,827,243 A | 10/1998 | Palestrant | |
| 5,893,869 A | 4/1999 | Barnhart et al. | |
| 5,941,869 A | 8/1999 | Patterson et al. | |
| 5,972,019 A | 10/1999 | Engelson et al. | |
| 6,066,149 A | 5/2000 | Samson et al. | |
| 6,159,195 A | 12/2000 | Ha et al. | |
| 6,183,492 B1 | 2/2001 | Hart et al. | |
| 6,206,868 B1 | 3/2001 | Parodi | |
| 6,238,412 B1 | 5/2001 | Dubrul et al. | |
| 6,280,464 B1 | 8/2001 | Hayashi | |
| 6,319,242 B1 | 11/2001 | Patterson et al. | |
| 6,350,271 B1 | 2/2002 | Kurz et al. | |
| 6,454,790 B1 | 9/2002 | Neuberger et al. | |
| 6,596,011 B2 | 7/2003 | Johnson et al. | |
| 6,626,886 B1 | 9/2003 | Barbut | |
| 6,632,236 B2 | 10/2003 | Hogendijk | |
| 6,679,893 B1 | 1/2004 | Tran | |
| 6,685,718 B1 | 2/2004 | Wyzgala et al. | |
| 6,685,722 B1 | 2/2004 | Rosenbluth et al. | |
| 6,692,504 B2 | 2/2004 | Kurz et al. | |
| 6,699,260 B2 | 3/2004 | Dubrul et al. | |
| 6,783,522 B2 | 8/2004 | Fischell | |
| 6,824,545 B2 | 11/2004 | Sepetka et al. | |
| 6,929,634 B2 | 8/2005 | Dorros et al. | |
| 7,008,434 B2 | 3/2006 | Kurz et al. | |
| 7,220,269 B1 | 5/2007 | Ansel et al. | |
| 7,232,452 B2 | 6/2007 | Adams et al. | |
| 7,252,674 B2 | 8/2007 | Wyzgala et al. | |
| 7,323,002 B2 | 1/2008 | Johnson et al. | |
| 7,374,561 B2 | 5/2008 | Barbut | |
| 7,399,307 B2 | 7/2008 | Evans et al. | |
| 7,645,261 B2 | 1/2010 | Hinchliffe | |
| 7,645,296 B2 | 1/2010 | Theron et al. | |
| 7,691,121 B2 | 4/2010 | Rosenbluth et al. | |
| 7,731,683 B2 | 6/2010 | Jang et al. | |
| 7,909,801 B2 | 3/2011 | Hinchliffe | |
| 8,100,935 B2 | 1/2012 | Rosenbluth et al. | |
| 8,162,878 B2 | 4/2012 | Bonnette et al. | |
| 8,292,914 B2 | 10/2012 | Morsi | |
| 8,409,237 B2 | 4/2013 | Galdonik et al. | |
| 8,425,549 B2 | 4/2013 | Lenker et al. | |
| 8,435,218 B2 | 5/2013 | Hinchliffe | |
| 8,475,487 B2 | 7/2013 | Bonnette et al. | |
| 8,486,104 B2 | 7/2013 | Samson et al. | |
| 8,784,441 B2 | 7/2014 | Rosenbluth et al. | |
| 8,911,468 B2 | 12/2014 | Ogle et al. | |
| 8,956,386 B2 | 2/2015 | Hauser et al. | |
| 8,979,870 B2 | 3/2015 | Richardson | |
| 9,067,063 B2 | 6/2015 | Chi et al. | |
| 9,427,252 B2 | 8/2016 | Sos | |
| 9,439,664 B2 | 9/2016 | Sos | |
| 9,566,412 B2 | 2/2017 | Ulm, III et al. | |
| 9,642,635 B2 | 5/2017 | Vale et al. | |
| 9,814,477 B2 | 11/2017 | Jensen | |
| 9,848,975 B2 | 12/2017 | Hauser | |
| 10,016,266 B2 | 7/2018 | Hauser | |
| 10,022,139 B2 | 7/2018 | Kobayashi et al. | |
| 10,076,399 B2 | 9/2018 | Davidson | |
| 10,080,575 B2 | 9/2018 | Brady et al. | |
| 10,105,154 B1 | 10/2018 | Green | |
| 10,130,387 B2 | 11/2018 | McRae et al. | |
| 10,231,751 B2 | 3/2019 | Sos | |
| 10,292,804 B2 | 5/2019 | Wang et al. | |
| 10,383,644 B2 | 8/2019 | Molaei et al. | |
| 10,433,867 B2 | 10/2019 | Kassab et al. | |
| 11,622,781 B2 | 4/2023 | Behan | |
| 11,737,767 B2 * | 8/2023 | Behan .................... | A61B 17/22 606/127 |
| 11,766,272 B2 | 9/2023 | Behan | |
| 11,911,057 B2 | 2/2024 | Behan | |
| 12,004,758 B2 * | 6/2024 | Behan .................. | A61B 17/221 |
| 2001/0011182 A1 | 8/2001 | Dubrul et al. | |
| 2002/0013548 A1 | 1/2002 | Hinchliffe | |
| 2002/0016624 A1 | 2/2002 | Patterson et al. | |
| 2002/0049452 A1 | 4/2002 | Kurz et al. | |
| 2002/0082558 A1 | 6/2002 | Samson et al. | |
| 2002/0188313 A1 | 12/2002 | Johnson et al. | |
| 2003/0200184 A1 | 10/2003 | Dominguez et al. | |
| 2004/0006306 A1 | 1/2004 | Evans et al. | |
| 2004/0006367 A1 | 1/2004 | Johnson et al. | |
| 2004/0049169 A1 | 3/2004 | Fischell | |
| 2004/0073243 A1 | 4/2004 | Sepetka et al. | |
| 2004/0127885 A1 | 7/2004 | Barbut | |
| 2004/0133232 A1 | 7/2004 | Rosenbluth et al. | |
| 2004/0153110 A1 | 8/2004 | Kurz et al. | |
| 2004/0158270 A1 | 8/2004 | Wyzgala et al. | |
| 2005/0027236 A1 | 2/2005 | Douk | |
| 2005/0197688 A1 | 9/2005 | Theron et al. | |
| 2005/0277976 A1 | 12/2005 | Galdonik et al. | |
| 2006/0041246 A1 | 2/2006 | Provost-Tine et al. | |
| 2006/0041304 A1 | 2/2006 | Jang et al. | |
| 2006/0189921 A1 | 8/2006 | Galdonik et al. | |
| 2006/0229645 A1 | 10/2006 | Bonnette et al. | |
| 2006/0264989 A1 | 11/2006 | Hinchliffe | |
| 2007/0207179 A1 | 9/2007 | Andersen et al. | |
| 2008/0015541 A1 | 1/2008 | Rosenbluth et al. | |
| 2008/0086110 A1 | 4/2008 | Galdonik et al. | |
| 2008/0103508 A1 | 5/2008 | Karakurum | |
| 2008/0312681 A1 | 12/2008 | Ansel et al. | |
| 2009/0156983 A1 | 6/2009 | Bonnette et al. | |
| 2009/0171267 A1 | 7/2009 | Bonnette et al. | |
| 2010/0082052 A1 | 4/2010 | Hinchliffe | |
| 2010/0131000 A1 | 5/2010 | Demello et al. | |
| 2010/0145371 A1 | 6/2010 | Rosenbluth et al. | |
| 2010/0222736 A1 | 9/2010 | Jang et al. | |
| 2010/0256600 A1 | 10/2010 | Ferrera | |
| 2011/0022075 A1 | 1/2011 | Christiansen et al. | |
| 2011/0060298 A1 | 3/2011 | Saadat | |
| 2011/0082493 A1 | 4/2011 | Samson et al. | |
| 2011/0130778 A1 | 6/2011 | Hinchliffe | |
| 2012/0022572 A1 | 1/2012 | Braun et al. | |
| 2012/0046676 A1 | 2/2012 | Morsi | |
| 2012/0271231 A1 | 10/2012 | Agrawal | |
| 2013/0190855 A1 | 7/2013 | Wang et al. | |
| 2014/0066969 A1 | 3/2014 | Eskridge | |
| 2014/0135803 A9 | 5/2014 | Rosenbluth et al. | |
| 2014/0200608 A1 | 7/2014 | Brady et al. | |
| 2014/0243790 A1 | 8/2014 | Callaghan et al. | |
| 2014/0257245 A1 | 9/2014 | Rosenbluth et al. | |
| 2014/0276403 A1 | 9/2014 | Follmer et al. | |
| 2014/0371769 A1 | 12/2014 | Vale et al. | |
| 2014/0371778 A1 | 12/2014 | Rudakov et al. | |
| 2015/0032147 A1 | 1/2015 | Janardhan et al. | |
| 2015/0088190 A1 | 3/2015 | Jensen | |
| 2015/0119895 A1 | 4/2015 | Tah et al. | |
| 2015/0250497 A1 | 9/2015 | Marks et al. | |

(56) References Cited

U.S. PATENT DOCUMENTS

| | | | |
|---|---|---|---|
| 2015/0359547 | A1 | 12/2015 | Vale et al. |
| 2016/0022296 | A1 | 1/2016 | Brady et al. |
| 2016/0249942 | A1 | 9/2016 | Olson |
| 2016/0249978 | A1 | 9/2016 | Lee et al. |
| 2016/0256180 | A1 | 9/2016 | Vale et al. |
| 2016/0271360 | A1 | 9/2016 | Ulm, III |
| 2016/0338720 | A1 | 11/2016 | Kassab et al. |
| 2016/0361077 | A1 | 12/2016 | Marks et al. |
| 2017/0105743 | A1 | 4/2017 | Vale et al. |
| 2017/0143938 | A1 | 5/2017 | Ogle et al. |
| 2017/0215903 | A1 | 8/2017 | Vale et al. |
| 2017/0238951 | A1 | 8/2017 | Yang et al. |
| 2017/0303949 | A1 | 10/2017 | Ribo Jacobi et al. |
| 2017/0333060 | A1 | 11/2017 | Panian |
| 2017/0333076 | A1 | 11/2017 | Bruzzi et al. |
| 2018/0104041 | A1 | 4/2018 | Hauser |
| 2018/0140315 | A1 | 5/2018 | Bowman et al. |
| 2018/0325647 | A1 | 11/2018 | Hauser |
| 2018/0333248 | A1 | 11/2018 | Davidson |
| 2018/0344248 | A1 | 12/2018 | Zeng et al. |
| 2019/0029713 | A1 | 1/2019 | McRae et al. |
| 2019/0133616 | A1 | 5/2019 | Sachar et al. |
| 2019/0133628 | A1 | 5/2019 | Follmer et al. |
| 2019/0167287 | A1 | 6/2019 | Vale et al. |
| 2019/0203032 | A1 | 7/2019 | Perry et al. |
| 2019/0269491 | A1 | 9/2019 | Jalgaonkar et al. |
| 2020/0281612 | A1 | 9/2020 | Kelly et al. |
| 2022/0061867 | A1 | 3/2022 | Jalgaonkar et al. |
| 2023/0233219 | A1 | 7/2023 | Behan et al. |
| 2025/0025192 | A1 | 1/2025 | Behan |

FOREIGN PATENT DOCUMENTS

| | | | |
|---|---|---|---|
| EP | 0385920 | A2 | 9/1990 |
| EP | 0561903 | A1 | 9/1993 |
| EP | 0630617 | A1 | 12/1994 |
| EP | 0561903 | B1 | 7/1995 |
| EP | 0820729 | A1 | 1/1998 |
| EP | 0630617 | B1 | 9/1998 |
| EP | 0961628 | A1 | 12/1999 |
| EP | 0961628 | A4 | 5/2000 |
| EP | 1007130 | A1 | 6/2000 |
| EP | 1007130 | A4 | 6/2000 |
| EP | 1007139 | A1 | 6/2000 |
| EP | 1007139 | A4 | 6/2000 |
| EP | 1026997 | A1 | 8/2000 |
| EP | 1030603 | A1 | 8/2000 |
| EP | 1105183 | A1 | 6/2001 |
| EP | 1105183 | A4 | 3/2002 |
| EP | 1241993 | A1 | 9/2002 |
| EP | 1304965 | A2 | 5/2003 |
| EP | 1030603 | A4 | 6/2003 |
| EP | 1355692 | A1 | 10/2003 |
| EP | 1408854 | A1 | 4/2004 |
| EP | 0961628 | B1 | 12/2004 |
| EP | 1561487 | A2 | 8/2005 |
| EP | 1561487 | A3 | 8/2005 |
| EP | 1026997 | B1 | 10/2005 |
| EP | 1355692 | A4 | 12/2005 |
| EP | 1105183 | B1 | 1/2006 |
| EP | 1611855 | A1 | 1/2006 |
| EP | 1677849 | A1 | 7/2006 |
| EP | 1007130 | B1 | 8/2006 |
| EP | 1691856 | A2 | 8/2006 |
| EP | 1696966 | A2 | 9/2006 |
| EP | 1241993 | B1 | 3/2007 |
| EP | 1761298 | A2 | 3/2007 |
| EP | 1561487 | B1 | 4/2007 |
| EP | 1789121 | A2 | 5/2007 |
| EP | 1791587 | A1 | 6/2007 |
| EP | 2208483 | A1 | 7/2010 |
| EP | 2319575 | A1 | 5/2011 |
| EP | 2786717 | A2 | 10/2014 |
| EP | 2786717 | A3 | 11/2014 |
| EP | 2848211 | A1 | 3/2015 |
| EP | 2851016 | A1 | 3/2015 |
| EP | 3017775 | A1 | 5/2016 |
| EP | 3020344 | A1 | 5/2016 |
| EP | 3718492 | A1 | 10/2020 |
| WO | WO-9306885 | A1 | 4/1993 |
| WO | WO-9823319 | A1 | 6/1998 |
| WO | WO-9823320 | A1 | 6/1998 |
| WO | WO-9834673 | A1 | 8/1998 |
| WO | WO-9836786 | A1 | 8/1998 |
| WO | WO-9916362 | A1 | 4/1999 |
| WO | WO-9923952 | A1 | 5/1999 |
| WO | WO-0012169 | A1 | 3/2000 |
| WO | WO-0145572 | A1 | 6/2001 |
| WO | WO-0187168 | A1 | 11/2001 |
| WO | WO-0209599 | A2 | 2/2002 |
| WO | WO-0239912 | A1 | 5/2002 |
| WO | WO-0209599 | A3 | 7/2002 |
| WO | WO-02055146 | A1 | 7/2002 |
| WO | WO-02087677 | A2 | 11/2002 |
| WO | WO-03097122 | A2 | 11/2003 |
| WO | WO-03097122 | A3 | 6/2004 |
| WO | WO-2005011786 | A1 | 2/2005 |
| WO | WO-2005039664 | A2 | 5/2005 |
| WO | WO-2005039664 | A3 | 6/2005 |
| WO | WO-2005046736 | A3 | 10/2005 |
| WO | WO-2005118050 | A2 | 12/2005 |
| WO | WO-2006023329 | A2 | 3/2006 |
| WO | WO-2006032686 | A1 | 3/2006 |
| WO | WO-2006023329 | A3 | 4/2006 |
| WO | WO-2006110186 | A2 | 10/2006 |
| WO | WO-2006110186 | A3 | 6/2007 |
| WO | WO-2008086180 | A1 | 7/2008 |
| WO | WO-2005118050 | A3 | 1/2009 |
| WO | WO-2009154441 | A1 | 12/2009 |
| WO | WO-2010075565 | A2 | 7/2010 |
| WO | WO-2011008987 | A3 | 5/2011 |
| WO | WO-2012156924 | A1 | 11/2012 |
| WO | WO-2014039548 | A1 | 3/2014 |
| WO | WO-2014113821 | A1 | 7/2014 |
| WO | WO-2014188300 | A1 | 11/2014 |
| WO | WO-2015189354 | A1 | 12/2015 |
| WO | WO-2016071524 | A1 | 5/2016 |
| WO | WO-2016113047 | A1 | 7/2016 |
| WO | WO-2016126974 | A1 | 8/2016 |
| WO | WO-2016138260 | A1 | 9/2016 |
| WO | WO-2016138508 | A1 | 9/2016 |
| WO | WO-2017074530 | A1 | 5/2017 |
| WO | WO-2017097616 | A1 | 6/2017 |
| WO | WO-2018033401 | A1 | 2/2018 |
| WO | WO-2018107133 | A1 | 6/2018 |
| WO | WO-2018107133 | A8 | 8/2018 |
| WO | WO-2018169959 | A1 | 9/2018 |
| WO | WO-2018222998 | A1 | 12/2018 |
| WO | WO-2019007032 | A1 | 1/2019 |
| WO | WO-2019027380 | A1 | 2/2019 |
| WO | WO-2019051425 | A1 | 3/2019 |
| WO | WO-2019094749 | A1 | 5/2019 |
| WO | WO-2019094782 | A1 | 5/2019 |
| WO | WO-2019168737 | A1 | 9/2019 |
| WO | WO-2021016213 | A1 | 1/2021 |
| WO | WO-2021151969 | A1 | 8/2021 |

OTHER PUBLICATIONS

Donkor, Eric., Stroke in the 21st Century: A Snapshot of the Burden, Epidemiology, and Quality of Life, Stroke Research and Treatment, vol. 2018, Article ID 3238165 (2018).

Extended European Search Report dated Sep. 27, 2019 in EP Patent Application Serial No. 19167604.8.

Froehler, Michael, Comparison of Vacuum Pressures and Forces Generated by Different Catheters and Pumps for Aspiration Thrombectomy in Acute Ischemic Stroke, Intervent. Neurol, 6(3-4):199-206 (May 2017).

Garcia-Tornel, et al., When to Stop: Detrimental Effect of Device Passes in Acute Ischemic Stroke Secondary to Large Vessel Occlusion, Stroke, 50(7):1781-1788 (Jul. 2019).

International Search Report & Written Opinion dated Jan. 10, 2025 in Int'l PCT Patent Appl. Serial No. PCT/IB2024/056942 (031001).

(56)                References Cited

OTHER PUBLICATIONS

International Search Report & Written Opinion dated Apr. 7, 2021 in Int'l PCT Patent Appl. Serial No. PCT/EP2021/051903 (011001).
International Search Report & Written Opinion dated Apr. 19, 2023 in Int'l PCT Patent Appl. Serial No. PCT/IB2023/050468 (021001).
Jin, et al., Association Between Extracranial Carotid Artery Tortuosity and Clinical Outcomes in Anterior Circulation Acute Ischemic Stroke Without Undergoing Endovascular Treatment, Journal of Stroke and Cerebrovascular Diseases, 29(2):104512 (Feb. 2020).
Kaymaz, et al., Influence of Carotid Tortuosity on Internal Carotid Artery Access Time in the Treatment of Acute Ischemic Stroke, Interventional Neuroradiology, 23(6):583-588 (Dec. 2017).
Mokin, et al., Semi-automated Measurement of Vascular Tortuosity and its Implications for Mechanical Thrombectomy Performance, Neuroradiology, 63(3):381-389 (Mar. 2021).
Mont'Alverne, et al., Unfavorable Vascular Anatomy During Endovascular Treatment of Stroke: Challenges and Bailout Strategies, Journal of Stroke: 22(2):185-202 (May 2020).
Pfaff, et al., Delivery Assist Catheters, a New Device Class and Initial Experience in Mechanical Thrombectomy in Acute Ischemic Stroke Patients, Clinical Neuroradiology, 29(4):661-667 (Dec. 2019).
Rosa, et al., Aortic and Supra-Aortic Arterial Tortuosity And Access Technique: Impact on Time to Device Deployment in Stroke Thrombectomy, Interventional Neuroradiology, 27(3):419-426 (Jun. 2021).
Sanchez, et al., ANCD Thrombectomy Device: In Vitro Evaluation, J. NeuroIntervent. Surg., 12(1):77-81 (Jan. 2020).
Snelling, et al., Unfavorable Vascular Anatomy Is Associated With Increased Revascularization Time and Worse Outcome in Anterior Circulation Thrombectomy, World Neurosurgery, 120:e976-83 (Dec. 2018).
Yeo, et al., Why Does Mechanical Thrombectomy in Large Vessel Occlusion Sometimes Fail?, Clinical Neuroradiology, 29(3):401-414 (Sep. 2019).
International Search Report & Written Opinion dated Sep. 12, 2025 in Int'l PCT Patent Appl. Serial No. PCT/IB2025/057533 (041001).

* cited by examiner

FIG. 3

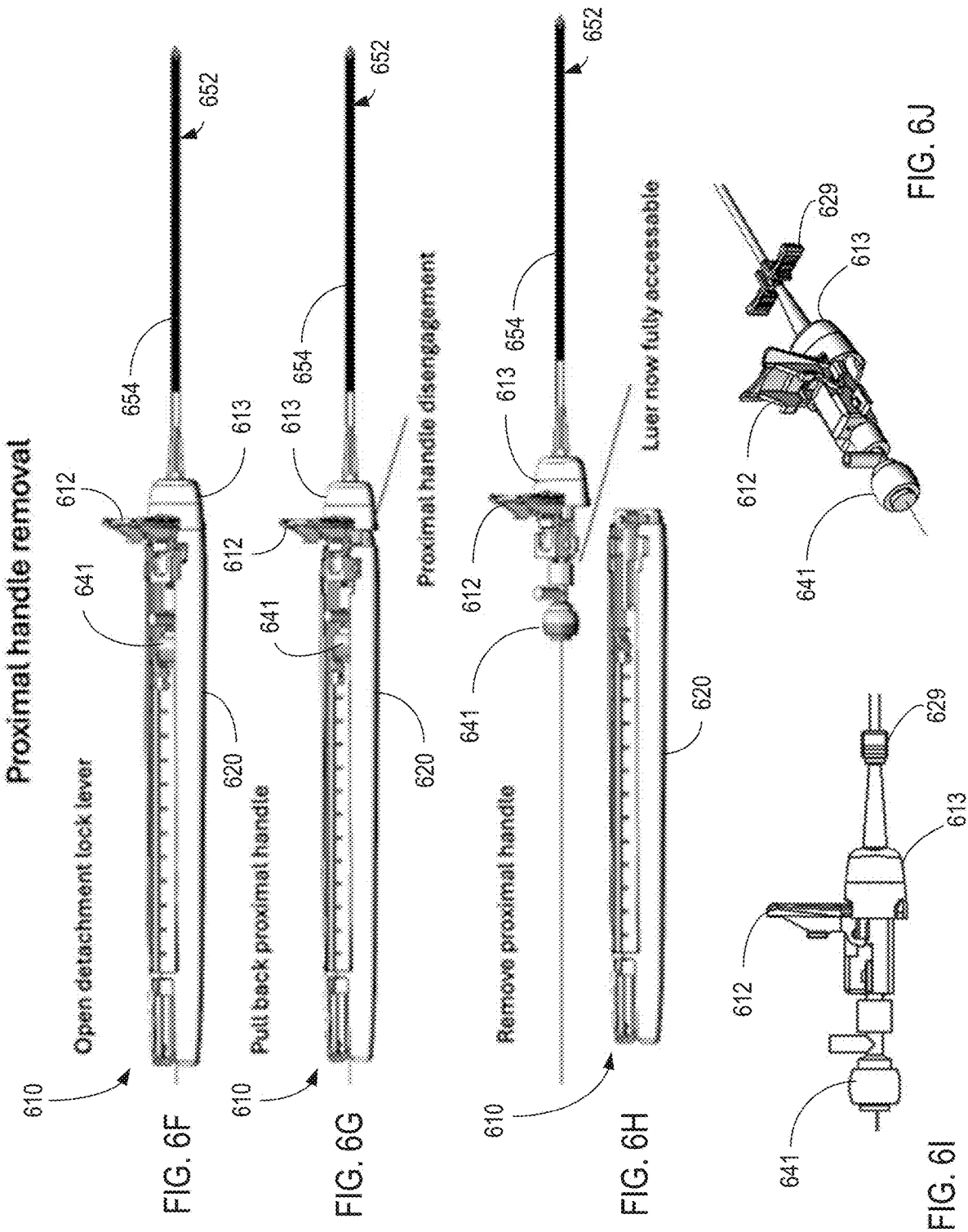

Connecting Nitinol Structure

Nitinol connector wire

Flat nitinol cap

1050

1008

1006

Marker bands

1004

1012

1002

1010

1016

1029

1034

1004

1006

1032

1012

1030

1016

1002

CATHETER SYSTEM WITH HIGHLY FLEXIBLE DISTAL PORTION FOR DISTAL ACCESS AND/OR CLOT REMOVAL

CROSS-REFERENCE TO RELATED APPLICATIONS

This application claims priority to European Patent Application No. EP 24306270.0, filed Jul. 26, 2024, the entire contents of which are incorporated herein by reference.

TECHNICAL FIELD

This technology generally relates to catheter systems for accessing blood vessels and/or removing an obstruction(s) from a blood vessel, for example, for retrieving a clot/thrombus in the neurovasculature for treatment of a stroke.

BACKGROUND

Ischemic stroke is caused by a partial or complete interruption to cerebral blood perfusion. Such an interruption may be caused by a thrombus or embolus, i.e. a clot, originating from a more proximal location within the bloodstream, becoming trapped within the narrowing intracranial vessels. The interruption of blood flow to a portion of the brain for any prolonged period of time results in a region of infarcted tissue, known as the core infarct, that is irreversibly damaged and grows larger with time. Infarcted regions of the brain will result in neurological deficits that may range from minor speech and coordination problems to total loss of muscle and cognitive control.

The oxygen-starved region around the core infarct also grows larger the longer the interruption continues. This region, known as the penumbra, may regenerate if blood perfusion is restored in a timely manner. This phenomenon of a treatable ischemic event has given rise to the phrase "time is brain," now common amongst associated clinicians.

In recent years, the technology for mechanical removal of such blockages has enabled reperfusion of blood flow and effective treatment of stroke in some cases. Within recent years, the first of several clinical studies were published that validated the efficacy of stent retrievers for blood flow restoration versus the standard of care at the time, which was intravenous thrombolysis medication and aspiration clot retrieval Mechanical clot retrieval devices are generally metal baskets or stents that are connected to a retrieval wire. During a clot removal procedure, a guide wire is placed across the length of the clot and a catheter is navigated over the guidewire to cross the clot. The clot retrieval device is delivered through the catheter to the required location. The catheter or sheath is retracted from over the clot retrieval device, which then expands and engages with the clot. The clot retrieval device and the clot integrated therein can then be removed through the blood vessel using tension by pulling the retrieval wire. Optionally, a suction catheter can be used to help with removal In many cases, the clot cannot be removed intact during the first pass of the clot retrieval device and multiple passes are required to get blood flow restoration. The improvement in first pass clot removal is a target of many current developments in this field of technology.

In practice, the clinician will use several different tools during the endovascular procedure to remove the clot. Generally, a guidewire will be placed into the femoral artery using the modified Seldinger technique and will be navigated through the carotid artery into the cerebral vasculature of the brain.

The guidewire is then pushed through the clot. Once the guidewire is in place, a very narrow tubular catheter known as a microcatheter (approx. 0.4 mm diameter) is advanced to the distal side of the clot over the wire.

The guidewire is then removed and a stent retriever is pushed through the microcatheter and deployed along the length of the clot. The stent retriever engages with the clot and is then retracted to remove the clot from the circulatory system of the patient. In most cases, this procedure is carried out while simultaneously applying aspiration through a larger diameter catheter that is navigated close to the clot over the microcatheter. The aspiration catheter is stiffer than the microcatheter due to its larger diameter and reinforcement, which is required to prevent collapse during suction. The microcatheter is therefore also required as a support and guide for introduction of the aspiration catheter through the vasculature.

European Patent Application Pub. No. EP 3718492 A1 discloses a catheter apparatus for the removal of a clot from the circulatory system of a patient in which a plurality of clot-engaging elements are deployable independently from each other. In this way, the first pass clot removal rate can be improved.

In addition to the above technique, there have been multiple different approaches described using the combination of stent retriever and aspiration catheter. Some of these techniques describe the complete withdrawal of stent retriever and clot into the aspiration catheter. Other approaches are directed to the withdrawal of the clot and stent retriever using the aspiration catheter, wherein the proximal part of the clot is attached to the aspiration catheter during the removal.

The clot retrieval approach chosen is often influenced by the clot composition and in some cases where the clot is very soft thrombus, an aspiration catheter alone may be sufficient to remove the entire clot via suction. In this case, a microcatheter is still required for support to help with navigation of the aspiration catheter to the desired site.

Regardless of the specific technique used, removal of the clot without delay is crucially important. Although the guidewire and microcatheter are generally advanced to the clot quickly, the positioning of the aspiration catheter may be a limiting factor. The process of advancing the aspiration catheter becomes particularly difficult after passing through the internal carotid artery. This is due to the narrow and tortuous vessels after this point in the cerebral vasculature and is exacerbated in older patients where the vasculature is diseased and elongated. This time-consuming part of the procedure may impact the patient's clinical outcome. In the case where the clot is not removed during the first pass, the cumulative time taken during multiple attempts can be significant.

Devices have been described with a distally expanding funnel at the distal end of the aspiration catheter. These devices are generally separate to the aspiration catheter and are fed through the lumen and pushed out of the distal end of the aspiration catheter to expand. Such devices are intended to widen the already large luminal diameter of the aspiration catheter and to engulf a withdrawing stent retriever and/or clot to ensure no microemboli are released during the clot removal. WO 02/087677 A2, U.S. Patent App. Pub. No. 2017/0303949 to Ribo Jacobi, WO 2016/113047 A1, U.S. Patent App. Pub. No. 2019/0269491 to Jalgaonkar, U.S. Patent App. Pub. No. 2017/0333060 to Panian are examples of documents directed to this kind of technique.

U.S. Pat. No. 6,632,236 to Hogendijk describes apparatus for occluding a vessel and enhancing blood flow within a catheter. The catheter includes a multi-section self-expanding wire weave forming a radially expandable body and an occlusive distal section, covered with an elastomeric polymeric coating, and disposed within an outer sheath.

U.S. Pat. No. 6,929,634 to Dorros describes apparatus and methods for treatment of stroke using a catheter having a distal occlusive member in the common carotid artery of the hemisphere of the cerebral occlusion. Retrograde flow is provided through the catheter to effectively control cerebral flow characteristics. Under such controlled flow conditions, a thrombectomy device is used to treat the occlusion, and any emboli generated are directed into the catheter.

U.S. Pat. No. 6,206,868 to Parodi discloses an occlusive element with a self-expanding wire mesh basket covered with an elastomeric polymer coating. The catheter is initially surrounded by a movable sheath, and is inserted transluminally with the sheath at a distalmost position. The sheath is retracted proximally to cause the basket to deploy, and the basket is again collapsed within the sheath by moving the sheath to its distal-most position.

U.S. Patent App. Pub. No. 2017/0238951 to Yang describes a neurovascular catheter for distal neurovascular access or aspiration. The catheter includes an elongate flexible tubular body, having a proximal end, a distal end, and a side wall defining a central lumen. A distal zone of the tubular body includes a tubular inner liner, a tie layer separated from the lumen by the inner liner, a helical coil surrounding the tie layer, an outer jacket surrounding the helical coil, and an opening at the distal end. Adjacent windings of the helical coil are spaced progressively further apart in the distal direction. The opening at the distal end of the tubular body is enlargeable from a first inside diameter for transluminal navigation to a second, larger inside diameter to facilitate aspiration of thrombus into the lumen.

U.S. Patent App. Pub. No. 2017/0143938 to Ogle describes a suction catheter system is described with a suction nozzle that can extend from a guide catheter of the like. The suction nozzle can be positioned by tracking the suction nozzle through a vessel while moving a proximal portion of the suction extension within the lumen of the guide catheter. A suction lumen extends from the proximal end of the guide catheter through at least part of the guide catheter central lumen and through the suction tip.

U.S. Patent App. Pub. No. 2016/0256180 to Vale describes a rapid exchange (RX) catheter that provides a proximal seal against a guide catheter inner lumen so that aspiration may be applied through a guide catheter. The catheter may include an exit port that defines a transfer port for aspiration and may enable minimal frictional engagement with the guide catheter proximal of the exit port. Aspiration can be applied to the lumen of the guide catheter and may be directed to and effective at the tip of the RX aspiration catheter. A tip of the RX catheter may facilitate aspiration and retrieval of the clot by expanding under load and can also partially or fully occlude the vessel.

WO 2017/097616 A1 discloses a plurality of devices and methods for removing blockages from blood vessels. A stent retriever is first deployed via a microcatheter and, to improve the clot removal process, an aspiration catheter is then advanced to the position of the clot. A clot receptor device is deployed, which circumferentially seals against a distal section of the aspiration catheter, such that the stent retriever and the clot may be aspirated through the tapered opening of the receptor device during the removal process. The stent retriever may also deployed using the microcatheter and an aspiration catheter is then forwarded to the position of the clot to aspirate the stent retriever and the clot.

U.S. Pat. No. 8,425,549 to Lenker discloses a catheter having a distal portion, which can be radially expanded by means of a coil or a helical ribbon that is distally displaceable within the catheter. The expanded configuration allows applying a negative pressure through the lumen of the catheter to aspirate obstructive matter through the distal end opening and into the lumen of the catheter.

Further devices for neurovascular endoluminal intervention of the kind as indicated are disclosed in WO 2016/126974, WO 2018/169959, and WO 98/23320.

Catheter devices have included radiopaque makers for guiding such devices to desired locations in the body. For example, U.S. Pat. No. 8,702,744 describes using a pattern of radio-opaque markers to guide positioning of a catheter device.

Besides the above-described catheter devices, introducer sheaths are known, which are short cannula-like devices that are used for vessel access. They are inserted into the target vessel percutaneously and a central dilator is then removed to allow access for insertion of other devices such as guidewires and catheters. Recently a number of introducer devices have been developed that have the capability to expand to accommodate devices larger than the nominal vessel size. Examples of expanding sheath type devices are the Edwards eSheath™ and the Terumo Solopath™.

For the foregoing reasons, quickly accessing a target site in the vasculature of a patient for delivery of a medical device and/or clot removal can be the difference between life and death. However, the vasculature often forms a tortuous path making it difficult to navigate catheters to distal locations in the vasculature. Complicating matters, accessing distal sites in the vasculature and introducing instruments often requires multiple devices and/or components each of which may involve numerous steps to ultimately deliver treatment. For example, different catheter system may be used for vasculature access and clot retrieval, requiring a number of orchestrated steps that must be performed in sequence to ultimately treat a patient.

Accordingly, there is a need for catheters and/or methods for efficiently navigating the vasculature of a patient for accessing a site in the vasculature and/or retrieving a clot or obstruction, and for efficiently deploying or otherwise introducing features or devices for treatment.

SUMMARY

Provided herein are systems and methods for distal access in a blood vessel to perform an intervention such as removing an obstruction(s) from the blood vessel. For example, an improved catheter is provided that is sufficiently small and flexible to permit navigation through small and/or tortuous vessels (e.g., the neurovasculature) while being sufficiently robust to remove an obstruction such as a clot/thrombus (e.g., via aspiration through the catheter). The catheter is designed to be easily expandable for obstruction removal and collapsible for delivery and removal within the vasculature.

In accordance with some aspects, a catheter is provided for removing an obstruction from a blood vessel. The catheter may include an elongated tube, an actuator tube disposed within the elongated tube, and an actuation wire disposed within the actuator tube. The elongated tube may be transitionable between an expanded state and a collapsed state. For example, the elongated tube may be sized and shaped to be advanced through the blood vessel to the obstruction in the collapsed state. The actuation wire may include an elongated shaft coupled to a plurality of struts via an articulation region. The distal end of each one of the plurality of struts may be affixed about a circumference of the distal end of the elongated tube. The actuator tube and the actuation wire may be used to transition the elongated tube between the collapsed and expanded states. For example, translation of the actuator tube relative to the actuation wire may cause the plurality of struts to expand radially outward to transition the elongated tube to the expanded state, thereby permitting removal of the obstruction from the blood vessel.

The elongated tube may include a braided material that may have an expandable biocompatible coating (e.g., an elastomer). The elongated tube may be collapsible via longitudinal force at the distal end of the elongated tube such that the elongated tube is longer in the collapsed state than in the expanded state.

The catheter may include an intermediate tube slidably positioned between the elongated tube and the actuator tube. The distal portion of the intermediate tube may be advanced distally within the elongated tube to reinforce the elongated tube for removal of the obstruction. A distal region of the intermediate tube may include a metal coil that may have a biocompatible coating.

The catheter may include a vacuum source to apply suction within the elongated tube to suck the obstruction into the elongated tube while in the expanded state to remove the obstruction from the blood vessel. For example, the vacuum source may be coupled to the intermediate tube that is disposed within the elongated tube during application of suction such that the obstruction is sucked into the lumen of the intermediate tube.

The actuator tube and the actuation wire may maintain the elongated tube in the collapsed state during delivery and also cause the elongated tube to transition from the expanded state to the collapsed state after removal of the obstruction from the blood vessel such that the catheter system is removable from a subject in the collapsed state. Each strut of the plurality of struts may have a curvature to facilitate even collapse of the actuation wire. In some embodiments, the curvature ensures that a distance from a distal tip of each strut to an apex of the actuation wire proximal to the plurality of struts is the same. The articulation region of the actuation wire may include a branched structure. Each strut of the plurality of struts may include an eyelet at a distal tip for coupling to the elongated tube. The elongated wire may be offset from a central longitudinal axis of the elongated tube in the expanded state. Distal ends of the plurality of struts may be spaced apart equidistant about the circumference of the distal end of the elongated tube. The actuation wire may be formed of nitinol.

The actuator tube may be a dual lumen microcatheter having a guidewire lumen configured to receive a guidewire. The guidewire lumen may extend more distally than an actuation lumen for the actuation wire in the actuator tube.

The distal end of the catheter may be sized and shaped to be navigated to the blood vessel within a brain. For example, the distal end of the catheter may be sized and shaped to be navigated to a middle cerebral artery within the brain.

In accordance with some aspects, a method for removing an obstruction from a blood vessel using a catheter is provided. The method may include advancing a distal end of an elongated tube in a collapsed state through a blood vessel to the obstruction while an actuator tube is disposed within the elongated tube; translating an actuator tube relative to an actuation wire to cause a plurality of struts of the actuation wire to expand radially outward to transition the elongated tube to an expanded state within the blood vessel, wherein a distal end of each one of the plurality of struts is affixed about a circumference of the distal end of the elongated tube; and removing the obstruction from the blood vessel using the elongated tube while in the expanded state. The method may include translating the actuator tube relative to the actuation wire to cause the plurality of struts of the actuation wire to collapse radially inward to transition the elongated tube to the collapsed state within the blood vessel. The method may include translating an intermediate tube within the lumen of the elongated tube (e.g., after the actuator tube has been removed from the elongated tube) such that the intermediate tube moves into the expanded distal region of the elongated tube to reinforce the distal region for obstruction removal (e.g., via aspiration).

In accordance with some aspects, another catheter is provided for removing an obstruction from a blood vessel. The catheter may include an elongated tube having a lumen and a distal end, the elongated tube designed to transition between an expanded state and a collapsed state, the elongated tube sized and shaped to be advanced through the blood vessel to the obstruction in the collapsed state, an actuator tube positioned within the elongated tube, and an actuation wire positioned within the actuator tube, the actuation wire including an elongated shaft, a connection structure including a plurality of struts, a proximal end of each one of the plurality of struts affixed about a circumference of the distal end of the elongated tube and a distal end of each one of the plurality of struts engaged with a distal end of the actuation wire. Translation of the actuator tube relative to the actuation wire may cause the plurality of struts to expand radially outward to transition the elongated tube to the expanded state, thereby permitting removal of the obstruction from the blood vessel.

In accordance with some aspects, another method for removing an obstruction from a blood vessel using a catheter is provided. The method may include advancing a distal end of an elongated tube in a collapsed state through a blood vessel to the obstruction while an actuator tube is disposed within the elongated tube, translating an actuator tube relative to an actuation wire to cause a plurality of struts engaged with the actuation wire and the elongated tube to expand radially outward to transition the elongated tube to an expanded state within the blood vessel, wherein a distal end of each one of the plurality of struts is affixed about a circumference of the distal end of the elongated tube, and removing the obstruction from the blood vessel using the elongated tube while in the expanded state.

In accordance with some aspects, a catheter system is provided for navigating to a distal site in a blood vessel. The catheter system may include an elongated tube having a lumen and a distal end, the elongated tube configured to transition between an expanded state and a collapsed state, a connection structure including a plurality of struts coupled to the distal end of the elongated tube, the plurality of struts biased to expand radially, an actuation wire engaged with the distal end of the elongated tube via the connection structure, and an actuator tube disposed within the elongated tube and configured to move axially with respect to the elongated tube to selectively engage the actuation wire, a handle including a handle body fixedly connected to the elongated tube, the handle including an actuator coupled to the actuator tube and designed to move with respect to the handle body to move the actuator tube with respect to elongated tube, wherein the actuator is configured to move the actuator tube distally to engage the distal end the actuator wire to cause the elongated tube to assume a contracted state.

In accordance with some aspects, a catheter system is provided for navigating to a target site in a blood vessel. The catheter system may include an elongated tube including a lumen and a distal end; the elongated tube configured to transition between an expanded state and a collapsed state, an actuation wire engaged with the distal end of the elongated tube; an intermediate tube disposed within the elongated tube and configured to move axially with respect to the elongated tube and the actuation wire; an actuator tube disposed within the elongated tube and configured to move axially with respect to the elongated tube to selectively engage the actuation wire to cause the elongated tube to transition between the expanded state and the collapsed state; and a handle coupled to the elongated tube, the handle including a first actuator coupled to the actuator tube and a second actuator coupled to the intermediate tube, the first actuator and second actuator configured to move with respect to the handle and with respect to one another, wherein the first actuator may be configured to releasably engage the second actuator to prevent the first actuator and the second actuator from moving with respect to the handle.

The actuator tube is prevented from moving with respect to the intermediate tube when the first actuator is engaged with the second actuator. The elongated tube is maintained in the collapsed state when the first actuator is engaged with the second actuator. The handle comprises a first channel and a second channel and the first actuator is positioned within the first channel and the second actuator is positioned within the second channel. The second actuator is configured to traverse the second channel. The first actuator is configured to be inserted into and removed from the first channel. The first actuator is compressible and is configured to be released from the second actuator and/or the handle when the first actuator is compressed. The first actuator and the second actuator are configured to releasably engage with one another via a snap or click engagement. The second actuator is coupled to a hemostasis valve in fluid communication with the intermediate tube. The second actuator, the intermediate tube, the elongated tube, and the hemostasis valve are configured to be removed from the handle.

In accordance with some aspects, a method is provided for accessing a blood vessel using a catheter coupled at a proximal end to a handle. The method may include causing an elongated tube of the catheter coupled to the handle to assume a contracted state by moving a first actuator of the handle along a first channel to a distal most position, the first actuator coupled to an actuator tube of the catheter disposed within the elongated tube and configured to move axially with respect to the elongated tube, the elongated tube coupled at a distal end of the elongated tube to an actuation wire disposed within the actuator tube; engaging the first actuator with a second actuator positioned along a second channel of the handle to lock an axial position of the actuator tube with respect to the elongated tube thereby locking the elongated tube in the collapsed state, the second actuator coupled to an intermediate tube disposed within the elongated tube; navigating a distal end of the catheter distally towards a target site in the blood vessel while the elongated tube is locked in the contracted state; and unlocking the first actuator from the second actuator and moving the first actuator proximally with respect the first channel to cause the elongated tube to transition from the contracted state to the expanded state at the target site.

The actuator tube is prevented from moving with respect to the intermediate tube when the first actuator is engaged with the second actuator. Unlocking the first actuator from the second actuator may include compressing the first actuator and moving the first actuator proximally with respect to the second actuator. Engaging the first actuator with a second actuator may include engaging a snap or click engagement. After unlocking the first actuator from the second actuator, the method may include advancing the second actuator along the second channel to move the intermediate tube distally while the elongated tube remains in the expanded state. The second actuator may be coupled to a hemostasis valve in fluid communication with the intermediate tube. The method may include connecting a vacuum source to the intermediate tube via the hemostasis valve. The actuator tube may include a first lumen and a second lumen and the actuation wire is disposed within the first lumen and a guidewire is disposed within the second lumen. A distal end of the first lumen is configured to engage a stopper positioned at a distal end of the actuation wire. The method may further include the first actuator of the handle along the first channel to a distal most position causes the actuation wire to move distally together with the actuator tube as the first lumen is engaged with the stopper of the actuation wire.

In accordance with some aspects, a catheter system is provided for accessing a target site in a blood vessel. The catheter system may include handle having a distal portion and a proximal portion removably coupled to the distal portion, the handle having a channel; an elongated tube coupled to the distal portion of the handle and configured to transition between an expanded state and a collapsed state; and an intermediate tube configured to be disposed within the elongated tube, the intermediate tube configured to move axially with respect to the elongated tube; an actuator coupled to the intermediate tube and configured to be positioned within the channel of the handle and to interface with the distal end of the handle while the actuator is in the channel, the actuator further configured to transition from an unlocked position to a locked position while interfacing with the distal end of the handle to couple the actuator to the distal portion of the handle; wherein the actuator and the distal end of the handle are configured to entirely disconnect from the proximal portion of the handle when the actuator is coupled to the distal portion of the handle.

A hemostasis valve may be coupled to a proximal end of the intermediate tube and in fluid communication with the intermediate tube. The hemostasis valve is configured to receive or interface with a treatment instrument and provide the treatment instrument access to an internal lumen of the intermediate tube. The hemostasis valve is configured to interface with a vacuum system configured for aspiration of an obstruction in the blood vessel. The hemostasis value is configured to be disconnected from the proximal end of the handle when the actuator and the distal end of the handle are entirely disconnected from the proximal portion of the handle. At least a portion of the actuator is configured to rotate to cause the actuator to transition from the unlocked position to the locked position. The proximal portion of the handle comprises at least one surface configured to resist movement of the handle when the handle is positioned upon a flat surface. The handle further comprises a second channel, the catheter system further including a second actuator positioned within the second channel and coupled to the actuator tube. A distal end of the actuator tube is configured to mechanically communicate with a distal end of the elongated tube. The method may include positioning the second actuator in a distal most position in the second channel causes the elongated tube to transition to the collapsed state.

In accordance with some aspects, a method is provided for accessing a target site in a blood vessel using a catheter. The method may include advancing a catheter including an elongated tube and an intermediate tube disposed within the elongated tube to the target site using a handle, the handle including a distal portion and a proximal portion removably coupled to the distal portion, the distal portion coupled to the elongated tube at a proximal end of the elongated tube; advancing, distally, an actuator in an unlocked position within a channel defined at least partially by the proximal portion of the handle until the actuator interfaces with the distal portion of the handle forming an end of the channel, the actuator coupled to the intermediate tube and configured to move the intermediate tube axially with respect to the elongated tube as the actuator moves within the channel; transitioning the actuator from the unlocked position to a locked position while the actuator is interfacing with the distal portion of the handle to couple the actuator to the distal portion of the handle and thereby prevent the elongated tube from moving axially with respect to the intermediate tube; and removing, entirely, the proximal portion of the handle from the distal portion of the handle while the actuator is coupled to the distal portion of the handle.

A hemostasis valve may be coupled to a proximal end of the intermediate tube and the hemostasis valve is configured to move with the actuator as the proximal portion of the handle is removed from the distal portion of the handle. The method may include connecting, after removing the proximal portion of the handle from the distal portion, a vacuum system to the hemostasis valve; and actuating the vacuum system for aspiration of an obstruction at the target site in the blood vessel. Transitioning the actuator from the unlocked position to a locked position may include rotating at least a portion of the actuator. The proximal portion of the handle may further define a second channel and a second actuator coupled to the actuator tube is positioned within the second channel. The method may include advancing distally, prior to advancing the catheter to the target site, the second actuator in the second channel to cause the second actuator and the actuator tube to move distally. The method may include locking the second actuator to the first actuator when the second actuator is in the distal-most position in the second channel and the actuator is in the proximal-most position in the channel such that the actuator is prevented from moving in the channel and the second actuator is prevented from moving in the second channel. The method may include compressing the second actuator, prior to advancing the actuator distally within the channel, to unlock the actuator from the second actuator. The method may include retracting the second actuator proximally in the second channel to cause the actuator tube to retract proximally thereby permitting the elongated tube to transition from a collapsed state to an expanded state. The actuator tube is configured to cause the elongated tube to transition between a collapsed state and an expanded state.

In accordance with some aspects, a catheter is provided for introduction into a blood vessel of a patient. The catheter may include an elongated tube including a lumen, a distal region, and a plurality of radiopaque markers positioned radially around a circumference of the distal region, the distal region sized and shaped to be advanced distally through the blood vessel in a collapsed state to a target site in the blood vessel such that the plurality of radiopaque markers are shown as a solid line under visualization in the collapsed state, wherein the distal region is configured to be expanded to an expanded state such that the plurality of radiopaque markers are shown as spaced apart under visualization.

The distal region may include a braid configured to transition between the collapsed state and the expanded state. The visualization may be fluoroscopy. The catheter further comprises an actuator wire mechanically engaged with the elongated tube via a connection structure. The connection structure may include a plurality of struts, a proximal end of each one of the plurality of struts affixed about a circumference of the distal region of the elongated tube and a distal end of each one of the plurality of struts engaged with the distal end of the actuation wire, and wherein distal translation of the actuation wire to a first position causes the plurality of struts to collapse radially inward to transition the elongated tube to the collapsed state. The method may further include proximal translation of the actuation wire to a second position proximal to the first position permits the elongated tube to transition to the expanded state. The connection structure is biased to cause the elongated tube to transition to the expanded state. The distal region of the elongated tube comprises a plurality of hoops and the proximal end of each one of the plurality of struts comprises a hook and wherein the hook of each one of the plurality of struts is configured to grasp a hoop of the plurality of hoops of the distal region of the elongated tube. The elongated tube further comprises a plurality of clips, each clip positioned over a hook of each one of the plurality of struts such that each hook is secured to a respective hoop of the plurality of hoops. Each radiopaque marker of the plurality of radiopaque markers is positioned on a respective clip of the plurality of clips.

In accordance with some aspects, a method is provided for introduction into a blood vessel of a patient. The method includes delivering an elongated tube including a lumen, a distal region, and a plurality of radiopaque markers positioned radially around a circumference of the distal region to a target site in the blood vessel of the patient while the elongated tube is in a collapsed state; causing an imaging system to generate at least one first medical image of the distal region of elongated tube at the target site while the elongated tube is in the collapsed state; expanding the distal region of the elongated tube while the distal region of the elongated tube is at the target site in the blood vessel of the patient such that the elongated tube achieves an expanded state at the target site; causing the imaging system to generate at least one second medical image of the distal region of elongated tube at the target site of the blood vessel when the elongated tube is in the expanded state, wherein in the at least one first medical image the plurality of radiopaque markers positioned radially around a circumference of the distal region of the elongated tube in the collapsed state appear as a solid line and in the at least one second medical image the plurality of radiopaque markers of the distal region in the expanded state appear spaced apart.

The distal region of the elongated tube comprises a braid configured to transition between the collapsed state and the expanded state. The imaging system is a fluoroscopy imaging system. An actuation wire is disposed within the elongated tube and is mechanically engaged with the distal region of the elongated tube. The actuator wire is mechanically engaged with the elongated tube via a connection structure including a plurality of struts, a proximal end of each one of the plurality of struts affixed about a circumference of the distal region of the elongated tube and a distal end of each one of the plurality of struts engaged with a distal end of the actuation wire, and wherein distal translation of the actuation wire to a first position causes the plurality of struts to collapse radially inward to transition the elongated tube to the collapsed state. Proximal translation of the actuation wire to a second position proximal to the first position permits the elongated tube to transition to the expanded state. The connection structure is biased to cause the elongated tube to transition to the expanded state. The distal region of the elongated tube comprises a plurality of hoops and the proximal end of each one of the plurality of struts comprises a hook and wherein the hook of each one of the plurality of struts is configured to grasp a hoop of the plurality of hoops of the distal region of the elongated tube. The elongated tube further comprises a plurality of clips, each clip positioned over a hook of each one of the plurality of struts such that each hook is secured to a respective hoop of the plurality of hoops at the proximal end of the elongated tube. Each radiopaque marker of the plurality of radiopaque markers is positioned on a respective clip of the plurality of clips.

In accordance with some aspects, a catheter is provided for introduction into a blood vessel of a patient. The catheter may include an elongated tube including a lumen and a distal end, the elongated tube configured to transition between an expanded state and a collapsed state, the elongated tube sized and shaped to be advanced distally through the blood vessel in the collapsed state to a target site in the blood vessel; an actuator tube configured to be disposed within the elongated tube; an actuation wire configured to be disposed within the actuator tube, the actuation wire including an elongated shaft having a distal end configured to extend distally past the distal end of the elongated tube; and a connection structure including a plurality of struts, a proximal end of each one of the plurality of struts affixed about a circumference of the distal end of the elongated tube and a distal end of each one of the plurality of struts engaged with the distal end of the actuation wire such that the distal end of the actuation wire extends distally beyond the elongated tube, wherein translation of the actuator tube relative to the actuation wire causes the plurality of struts to expand radially outward to transition the elongated tube to the expanded state.

The connection structure may be biased to expand radially. The actuation wire may include a stopper at the distal end of the actuation wire. The connection structure may include a void through which the actuation wire traverses and the stopper at the distal end of the actuation wire is larger than the void. The connection structure may include a disk structure in which the void is positioned and the distal end of each one of the plurality of struts is coupled to the disk structure. A portion of the connection structure may be positioned between a distal end of the actuator tube and the stopper of the actuation wire and distal translation of the actuation tube causes the connection structure to move distally to cause the elongated tube to transition to a collapsed state. The proximal translation of the actuation tube may permit the connection structure to move proximally thereby permitting the elongated tube to expand. The connection structure may include a plurality of radiopaque markers. The elongated tube may be coupled to a handle and the actuator tube may be coupled to an actuator movably coupled to the handle and configured to move within the handle to cause the actuator tube to move. Movement of the actuator causes the actuator tube to move with respect to the elongated tube.

In accordance with some aspects, a method is provided for accessing a blood vessel using a catheter including an elongated tube, an actuation tube, and an actuation wire. The method may include advancing in a distal direction a distal end of the elongated tube in a collapsed state through a blood vessel to a target site within the blood vessel while the actuator tube is disposed within the elongated tube and the actuator wire is disposed within the actuator tube; translating the actuator tube relative to the actuation wire to cause a plurality of struts engaged with both the actuation wire and the elongated tube to expand radially outward to transition the elongated tube to an expanded state within the blood vessel, wherein a distal end of the actuation wire extends distally past a distal end of the elongated tube and each one of the plurality of struts extends from the distal end of the actuation wire proximally towards the distal end of the elongated tube, each one of the plurality of struts including a proximal end that is affixed to a circumference of the distal end of the elongated tube and a distal end that is engaged with the distal end of the actuation wire; and performing an intervention within the blood vessel at the target site using the elongated tube while in the expanded state.

The plurality of struts may be biased to expand radially. The actuation wire may include a stopper at the distal end of the actuation wire. The plurality of struts may form at least a portion of a connection structure and the connection structure comprises a void through which the actuation wire traverses and wherein the stopper at the distal end of the actuation wire is larger than the void. The connection structure may include a disk structure in which the void is positioned and the distal end of each one of the plurality of struts is coupled to the disk structure. A portion of the connection structure may be positioned between a distal end of the actuator tube and the stopper. The method may further Translating the actuator tube distally relative to the actuation wire causes the connection structure to move distally to cause the elongated tube to transition to the collapsed state. The method may further include translating the actuator tube proximally relative to the actuation wire permits the connection structure to move proximally to permit the elongated tube to transition to the expanded state. The elongated tube is coupled to a handle and the actuator tube is coupled to an actuator movably coupled to the handle and configured to move within the handle to cause the actuator tube to move. Movement of the actuator may cause the actuator tube to move with respect to the elongated tube.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

The foregoing and other objects, features, and advantages of the description set forth herein will be apparent from the following description of particular embodiments of those inventive concepts, as illustrated in the accompanying drawings. It should be noted that the drawings are not necessarily to scale; emphasis instead is placed on illustrating the principles of the inventive concepts. Also, in the drawings, like reference characters may refer to the same parts or similar parts throughout the different views. It is intended that the embodiments and figures disclosed herein are to be considered illustrative rather than limiting.

FIG. 3 shows exemplary steps for self-collapsing the collapsible portion of the elongated tube using an actuator tube and actuation wire system.

FIGS. 6A-6H show an exemplary method for manipulating the catheter system using the handle to transition the elongated tube from the collapsed state to the expanded state and extending the intermediate tube distally.

FIGS. 6I and 6J illustrate a distal end and actuator of the handle entirely disconnected from the proximal end of the handle, while the elongated tube and intermediate tube, as well as hemostasis valve, remain connected to the distal end of the handle and the actuator.

DETAILED DESCRIPTION

Provided herein are systems and methods for accessing a distal site in a patient's vasculature and/or removing an obstruction(s) from the patient's vasculature. For example, an improved catheter may be used for the treatment of ischemic stroke, which allows an overall easier and faster removal of a clot from a blood vessel. In another example, an improved catheter may be used for accessing a site in the patient's vasculature and delivering a medical device or other treatment.

The catheter has a collapsed state where the distal outer section is adapted to be easily navigated through the vasculature including through small and/or tortuous vessels (e.g., the neurovasculature). The catheter may then, preferably reversibly, be changed to an expanded state whereby the distal outer section is expanded to a wider diameter, which may be approximately equivalent to the diameter of the proximal outer section. This approach enables the catheter to be easily and rapidly navigated to the target site and subsequently dilated for access to a distal site in the patient's vasculature and/or to facilitate removal of the one or several clots by aspiration. Using this design, a clinician does not waste valuable time navigating a large aspiration catheter through tortuous vessels. In addition, a microcatheter and an aspiration catheter may be combined into a single catheter, which also represents cost savings.

Figure 1A:
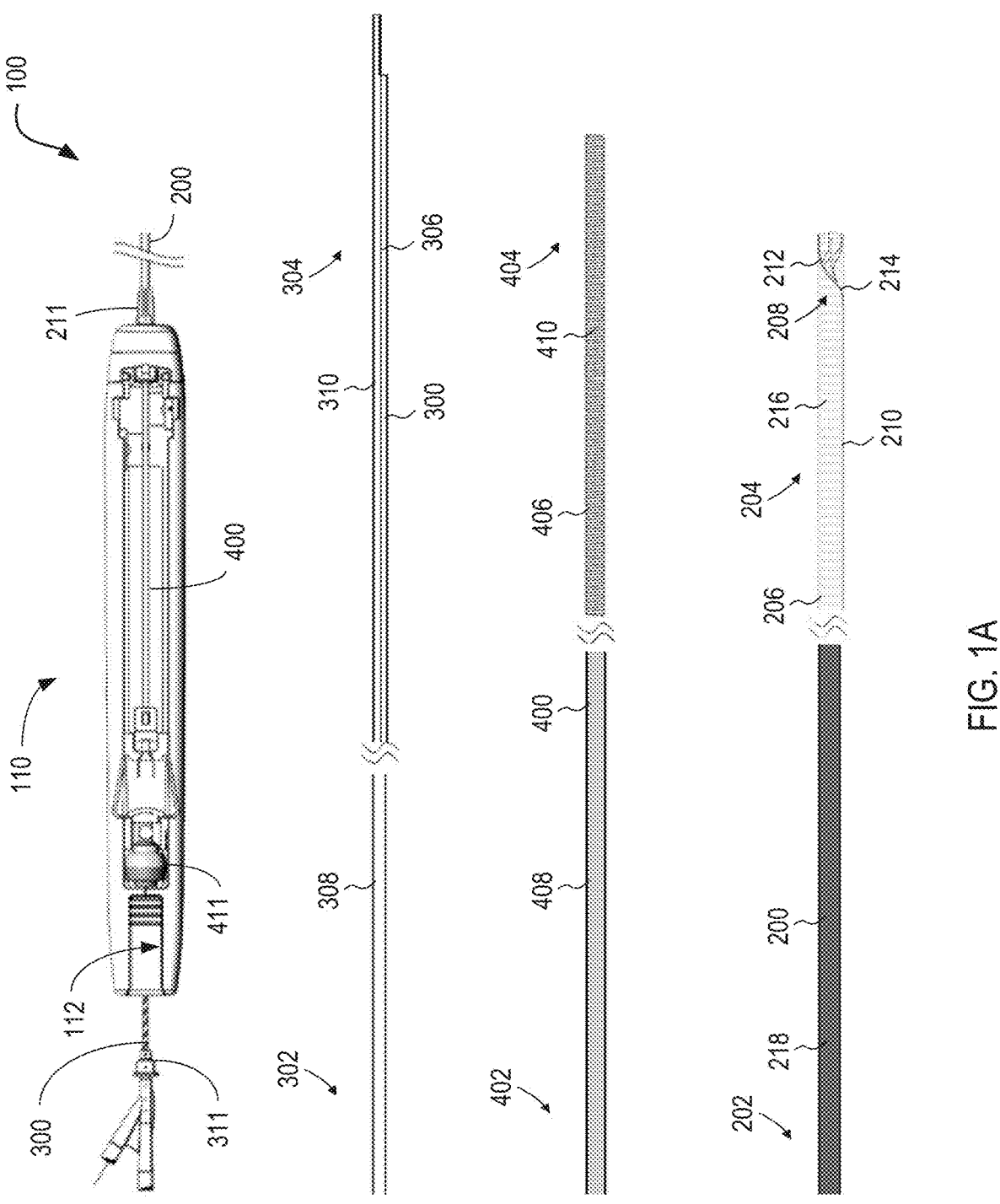
FIG. 1A shows exemplary components of a catheter for accessing a distal site and/or removing an obstruction(s) from a blood vessel.

Referring to FIG. 1A, an exemplary catheter system is shown that may be used for accessing the vasculature for performing an intervention such as removing an obstruction (s) from a blood vessel, for example, to treat a stroke. The various shafts/tubes of the catheters incorporate features from the catheters described in U.S. Pat. No. 11,737,767 to Behan and Grandidier and/or U.S. Pat. No. 11,622,781 to Behan, the entire contents of each of which are incorporated by reference herein. Catheter system 100 illustratively includes handle 110, elongated tube 200 that connected to handle 110 and is transitionable between an expanded state and a collapsed state. Elongated tube 200 has proximal region 202, distal region 204, and lumen 206 extending therebetween. Elongated tube 200 is connected to handle 110 at the proximal end and is sized and shaped to be advanced through the blood vessel to a desired site in the vasculature (e.g., the site of an obstruction in the collapsed state).

To transition elongated tube 200 between the collapsed state and the expanded state, actuation wire 208 is provided. As illustrated, actuation wire 208 may include elongated shaft 210 coupled to a plurality of struts 212 via articulation region 214. The distal end of each one of the plurality of struts 212 may be affixed about a circumference of the distal end of elongated tube 200. Actuation wire 208 preferably has a length longer than elongated tube 200. As such, actuation wire 208 may be coupled to the distal end of elongated tube and extend out the proximal end, as shown in FIG. 1A, for manipulation by the clinician.

The portion of elongated tube 200 at distal region 204 is preferably formed of a contractible and expandable material such as a coil, a laser-cut tube, or braid 216 as illustrated. Distal region 204 may be coated (e.g., one side or both sides) with an expandable biocompatible material such as an elastomer. For example, the collapsible/expandable portion of elongated tube 200 may be an elastomer coated braid or coil. The coating(s) may be made in the manner described in U.S. Patent Application Pub. No. 2025/0025192 to Behan, the entire contents of which are incorporated herein by reference. Proximal region 202 may be formed of a different material than distal region 204. For example, proximal region 202 may include shaft 218 formed from a polymer known in the art of catheter design. The diameter of proximal region 202 may be fixed such that only distal region 204 has a variable diameter. The elastomer coated braid or coil may be bonded to proximal region 202, for example, via an adhesive. Elongated tube 200 may include hemostasis valve 211 at the proximal end to close off proximal end of lumen 206 when the hemostasis valve is closed. For example, hemostasis valve 211 may be incorporated into handle 110 or the proximal end of elongated tube 200.

Preferably, shaft 218 of elongated tube 200 is flexible. Distal region 204 (illustratively, braid 216) is particularly flexible to permit navigation through the vasculature, including through small and/or tortuous vessels.

Catheter system 100 further may include actuator tube 300, which is sized and shaped to be disposed within elongated tube 200. Actuator tube 300 includes proximal region 302, distal region 304, and lumen 306 extending therebetween. Lumen 306 is sized and shaped to receive actuation wire 208 therethrough. Preferably, actuator tube 300 has a length longer than the shaft of elongated tube 200, although actuation wire 208 is preferably longer than actuator tube 300.

Actuator tube 300 may be connected at handle 110 to actuator 112, which may be designed to slide along handle 110. Actuator tube 300 may be moved by moving actuator 112 and may work together with actuation wire 208 to cause distal region 204 of elongated tube 200 to transition between the collapsed state and the expanded state. This provides a self-collapsing mechanism for easy and repeatable transition between these states. For example, actuator 112 may be moved proximally to cause actuator tube 300 to move proximally, resulting in translation of actuation wire 208 relative to actuator tube 300 to cause the plurality of struts 212 to expand radially outward to transition elongated tube 200 to the expanded state. In the expanded state, elongated tube may permit access to a distal site in the vasculature and/or removal of an obstruction from the blood vessel.

Actuator tube 300 may function as a microcatheter. Shaft 308 at proximal region 302 may be relatively stiff (e.g., actuator tube 300 may be a hypotube). The diameter of actuator tube 300 may be fixed such that actuator tube 300 is not expandable. Distal region 304 may preferably be more flexible than proximal region to permit bending and navigation through tortuous vessels. Actuator tube 300 may include guidewire lumen 310 to receive a guidewire therethrough. As illustrated, actuator tube 300 may be a dual lumen microcatheter having both guidewire lumen 310 and lumen 306 for receiving actuation wire 208 there through. Guidewire lumen 310 may extend more distally in the shaft than actuation lumen 306 for actuation wire 208 in actuator tube 300.

Actuator tube 300 may include hemostasis valve 311 at the proximal end to permit insertion of additional interventional devices (e.g., guidewire, actuation wire) into a lumen (s) of actuator tube 300 and to close off proximal end of lumens 306 and/or 310 when hemostasis valve 312 is closed.

Catheter system 100 further may include intermediate tube 400, which is sized and shaped to be disposed within elongated tube 200. Intermediate tube 400 includes proximal region 402, distal region 404, and lumen 406 extending therebetween. Lumen 406 is sized and shaped to receive actuator tube 300 therethrough and to fit within intermediate tube 200. Preferably, intermediate tube 400 has a length less than actuator tube 300, but longer than the shaft of elongated tube 200, although actuation wire 208 is preferably longer than intermediate tube 400.

Intermediate tube 400 is slidably disposed within elongated tube 200. For example, the distal end of intermediate tube 400 may be positioned proximally to the distal end of elongated tube 200 during delivery so as to maintain the low profile of catheter 200. Once suitable positioning is achieved in proximity to the obstruction in the blood vessel and elongated tube 200 has been transitioned to the expanded state, intermediate tube 400 may be advanced distally within elongated tube 200 to reinforce elongated tube 200 for removal of the obstruction.

Proximal region 402 may be formed of a different material than distal region 404. For example, proximal region 402 may include shaft 408 formed from a polymer known in the art of catheter design to provide flexibility. Distal region 404 may include a tube 410 (e.g., a coil or hypotube made from biocompatible metal such as nitinol or stainless steel). Tube 410 may have a biocompatible coating (e.g., PTFE). In one example, tube 410 may be a laser cut hypotube. In another example, tube 410 may be a tightly wound coil such that adjacent turns in the coil contact one another. The diameter of intermediate tube 400 may be fixed such that intermediate tube 400 is not expandable. Intermediate tube 400 may include hemostasis valve 411 at the proximal end, which may be inserted into and/or move with respect to handle 110. Hemostasis valve 411 may permit insertion of additional interventional devices (e.g., actuator tube 300) into lumen 406 of intermediate tube 400 and/or may close off the proximal end of lumen 406 when hemostasis valve 411 is closed. One or more additional valves may be connected to the proximal end of intermediate catheter 400, for example, to permit coupling to a vacuum source for aspiration of the obstruction in the blood vessel via catheter system 100.

Figures 1B, 1C:
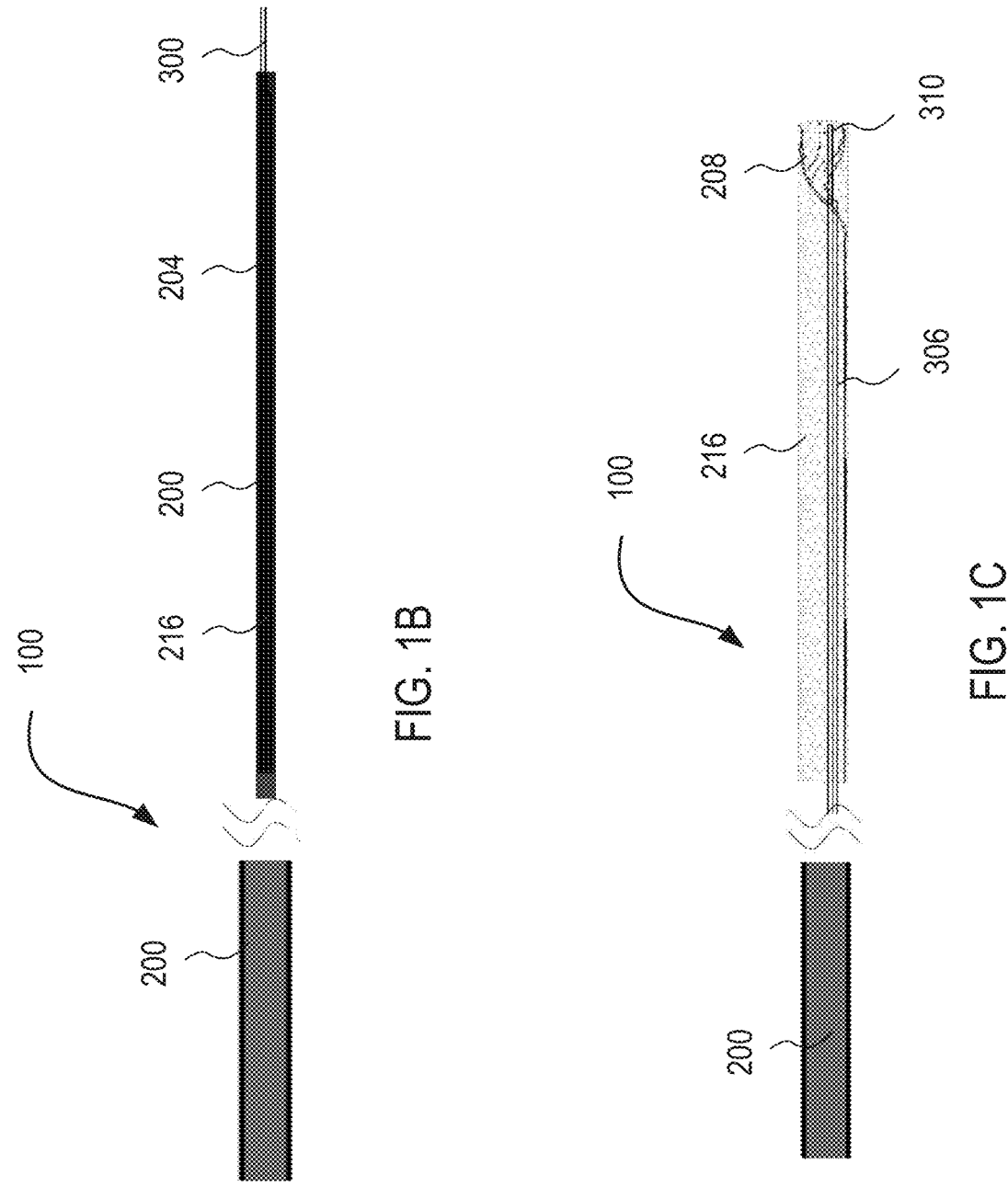
FIGS. 1B and 1C show, respectively, the catheter in the collapsed state and the expanded state.

Referring now to FIGS. 1B and 1C, the distal end of catheter system 100 is shown, respectively, in a collapsed state and an expanded state. In the collapsed state illustrated in FIG. 1B, actuator tube 300 is advanced distally to cause catheter system to assume the collapsed state. In FIG. 1C, actuator tube 300 is retracted proximally to permit catheter system 100 to transition from the collapsed state to the expanded state. Actuator tube 300 may be moved in one direction (e.g., proximally) relative to actuation wire 208 to actuate the transition from collapsed to expanded and may be moved in another direction (e.g., distally) relative to actuation wire 208 to actuate the transition from the expanded to the collapsed state. For example, actuator tube 300 may be unlocked by the clinician and moved proximally while elongated shaft 200 and intermediate tube 400 remain in place to cause distal region 204 (e.g., braid 216) of elongated shaft to expand. As such, elongated tube 200 is collapsible via longitudinal force at the distal end of elongated tube 200. As shown, elongated tube 200 is longer in the collapsed state than in the expanded state.

In this manner, the braided distal end of catheter system 100 may be collapsed by being elongated. Braid elongation may be generally achieved by applying a longitudinal force to the distal end of the braided section. Conversely, the braid expansion may be achieved by releasing the longitudinal force. Advantageously, the distal end of elongated tube 200 may be held in place during expansion to prevent the catheter tip from jumping back upon the release of force. The self-collapsing mechanism allows force to be applied to the distal end of the braid as well as holding the distal end in place during expansion. As further advantages, these mechanisms allow advancing actuator tube 300 (e.g., a microcatheter) towards the distal end of elongated tube 200 to taper the diameter of the distal lumen and using actuator tube 300 to subsequently elongate braid 216 to narrow/ collapse the entire distal braided section. As such, braid 216 may be collapsed onto actuator tube 300 to provide the sizing and flexibility of a microcatheter for delivery and removal of the distal end of catheter system 100.

Catheter system 100 is preferably adapted to be inserted into the femoral artery of an adult human patient and to be navigated to the brain, for example to the middle cerebral artery, of the patient. Thus, the length of the catheter is preferably such that the catheter at least extends from the femoral artery of an adult human patient to the brain, in particular to the middle cerebral artery, of the same patient, to outside the patient for manipulation at the proximal end by the clinician. Depending on the application (e.g. in animals or humans, in children, female or male adults, etc.), catheter system 100 preferably has an overall length of at least 30 cm, more preferably of at least 40 cm. For the use in humans, in particular in adult humans, the overall length of the catheter is preferably in a range between 100 cm and 200 cm, more preferably in a range between 130 cm and 180 cm.

The sizing of catheter system 100 may be optimized for navigation in the neurovasculature. For example, the outer diameter of the shape-changing section distal section (e.g., the braided section) of elongated tube may be 0.5-6 mm in the collapsed state and 1-10 mm in the expanded state. In addition, the length of the shape-changing section distal section of elongated tube may be at least 10 cm from the distal end of elongated tube 200, such as 10-25 cm total, and may reduce about 5-25% in length when transitioned to the expanded state as compared to the collapsed state. In some embodiments, the diameter at the distal region of actuator tube 300 may be 0.4-2 mm for the dual lumen microcatheter configuration. The outer diameter of intermediate tube 400 may be 1-10 mm with an inner diameter of 0.8-8 mm. The length of the coiled section of intermediate tube 400 may extend at least 10 cm from the distal end of intermediate tube 400.

Figures 2A, 2B, 2C, 2D:
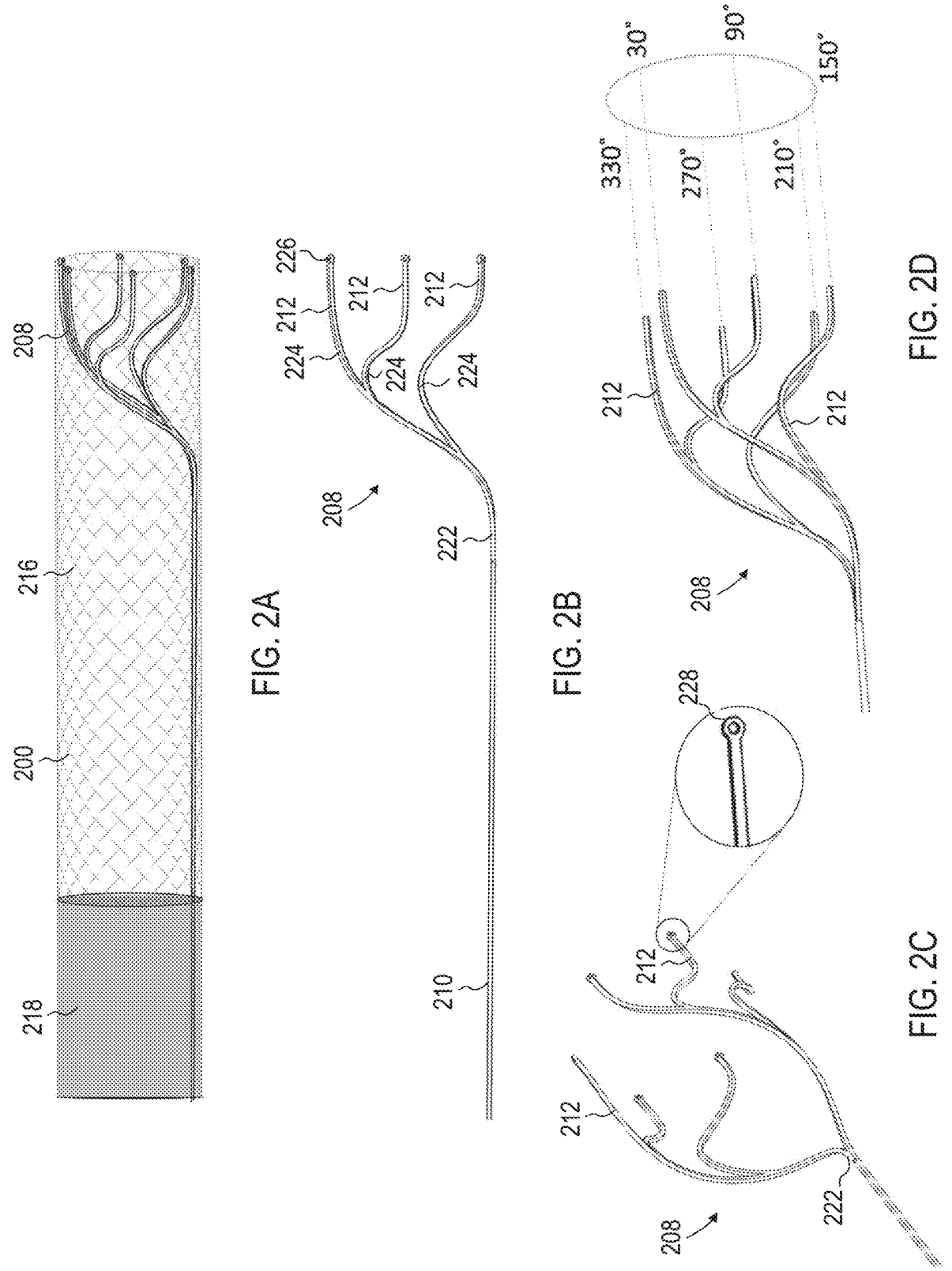
FIG. 2A shows the distal region of an elongated tube of the catheter for an exemplary embodiment having a collapsible and expandable braided section using a self-collapsing/expanding mechanism.
FIG. 2B shows the distal region of an exemplary mechanism for self-collapsing/expanding the distal region (e.g., the braided section) of the elongated tube.
FIGS. 2C and 2D are perspective views of the exemplary mechanism of FIG. 2B.

Referring now to FIG. 2A, a view of an exemplary distal region of elongated tube 200 is shown. Elongated tube 200 may include braid 216 at the distal end and shaft 218 coupled to braid 216 more proximally. Actuation wire 208 is shown to facilitate self-collapse/expansion of the distal end of elongated tube 200 (e.g., the entire braided section). In some embodiments, the self-collapse/expansion mechanism (actuation wire 208) is mounted to the distal end of the braided structure to facilitate a reduction in the braid diameter by enabling the clinician to both collapse the distal braid and to elongate the braid by applying a force longitudinally to the distal end of the braid.

FIG. 2B shows the distal region of an exemplary mechanism for self-collapsing the distal region of the elongated tube. Actuation wire 208 illustratively includes elongated shaft 210 coupled to struts 212 via articulation region 214. Actuation wire 208 may be formed from biocompatible metal such as nitinol or stainless steel and may exhibit shape memory characteristics. In some embodiments, actuation wire 208 is formed from nitinol wire. Actuation wire 208 may be formed of nitinol wire with distal multi-armed nitinol, as shown. Actuation wire 208 may be formed from a single piece of nitinol or from a plurality of nitinol pieces coupled together. For example, struts 212 may be laser cut from a single nitinol tube and coupled to the nitinol wire at apex 222, for example, via welding. Struts 212 may be configured to self-expand when actuated, for example, when exposed from the lumen of the actuator tube. Each strut 212 may have curvature 224 to facilitate even collapse of actuation wire 208. In some embodiments, curvature 224 of each strut 212 ensures that the distance from distal tip 226 of each strut 212 to apex 222 of actuation wire 208 is the same. Apex 222 preferably begins proximal to plurality of struts 212. Struts 212 may each have an S-shape. For example, the upper-most struts may form an S-shape with elongated shaft 210 and have one or more additional struts branch off the upper-most struts in S-shape form, as shown. There may be multiple upper-most struts, for example, two as shown in FIG. 2C. In some embodiments, struts 212 to not make a complete circle around the circumference at the distal end of the elongated tube. For example, there may be a gap between the struts (e.g., upper-most struts shown in FIG. 2C). In this manner, articulation region 214 may have a branched structure and, in some embodiments, the branches have multiple branches extending therefrom forming their own distinct networks of branches.

Referring now to FIG. 2C, a perspective view of the distal region of actuation wire 208 is shown. Struts 212 may be arranged circumferentially to connect to the inner lumen of the elongated tube (e.g., the braid). Elongated shaft 210 may be offset from a central longitudinal axis of the elongated tube in the expanded state. This ensures that elongated shaft 210 does not occlude the lumen of the elongated tube. Each strut 212 may include a coupling mechanism to couple to the distal end of the elongated tube. For example, each strut 212 may include eyelet 228 at its distal tip to facilitate connection to the braid.

As shown in FIG. 2D, distal ends of struts 212 may be spaced apart equidistant such that the struts are spaced apart about the circumference of the distal end of the elongated tube. As illustrated, there may be six struts spaced apart 60 degrees from one another. It will be understood by one of ordinary skill in the art that actuation wire 208 and struts 224 and 212 may alternatively be the actuation wire and connection structure in FIGS. 10A-10G.

Figure 3:
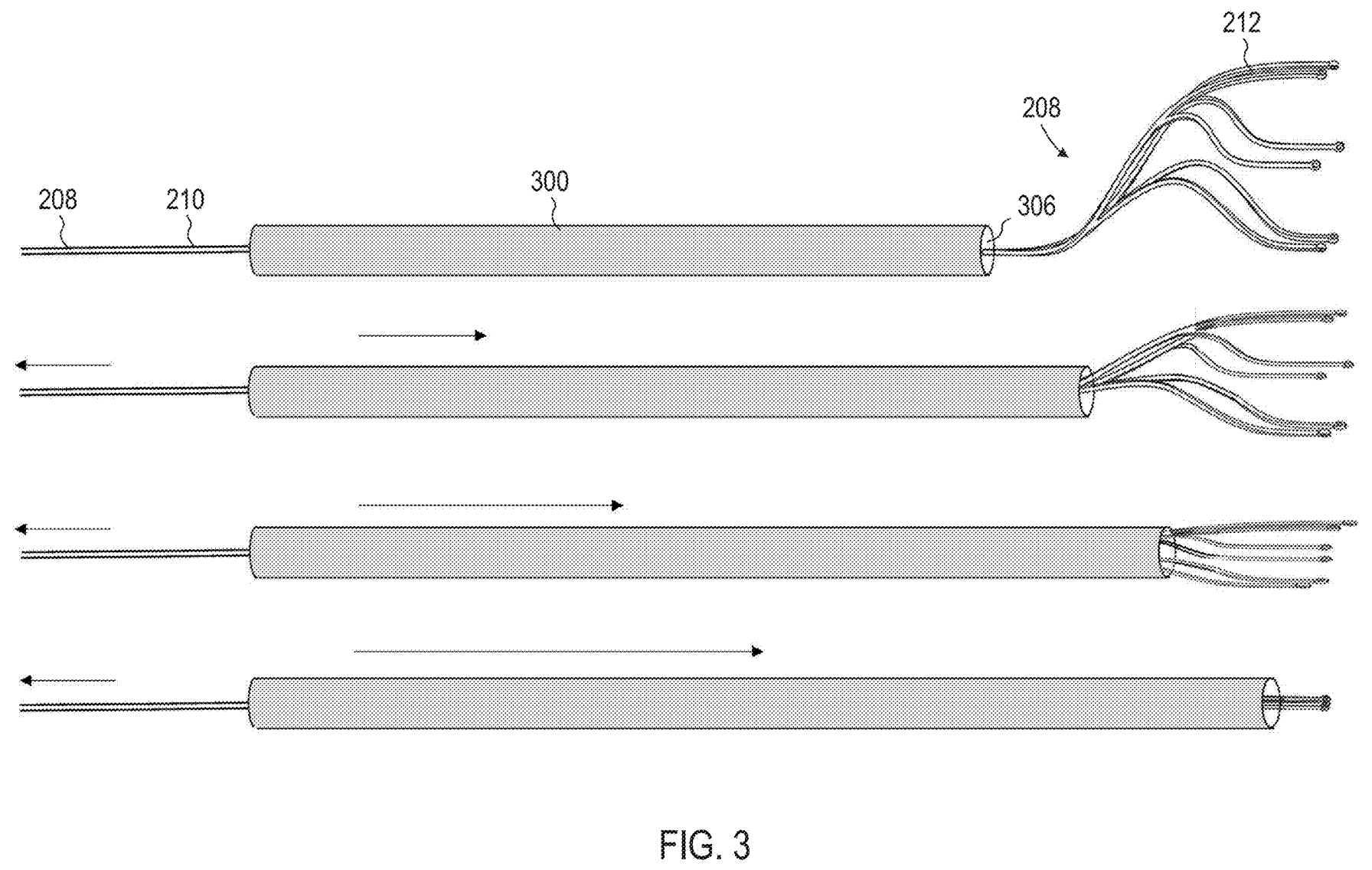

FIG. 3 illustrates exemplary steps for collapsing the distal end of elongated tube 200 using the actuation mechanisms. For example, as actuator tube 300 is advanced relative actuation wire 208, actuation wire 208 is drawn into lumen 306 of actuator tube 300. This causes the distal multi-armed strut structure to collapse radially inwards to transition to the collapsed state. As shown, curvature in the struts ensures equal circumferential collapse force. Actuator tube 300 may be advanced distally while actuation wire 208 is held in place, actuation wire 208 may be moved proximally while actuator tube is held in place, or actuator tube 300 may be advanced distally while actuation wire 208 is moved proximally.

Figure 4:
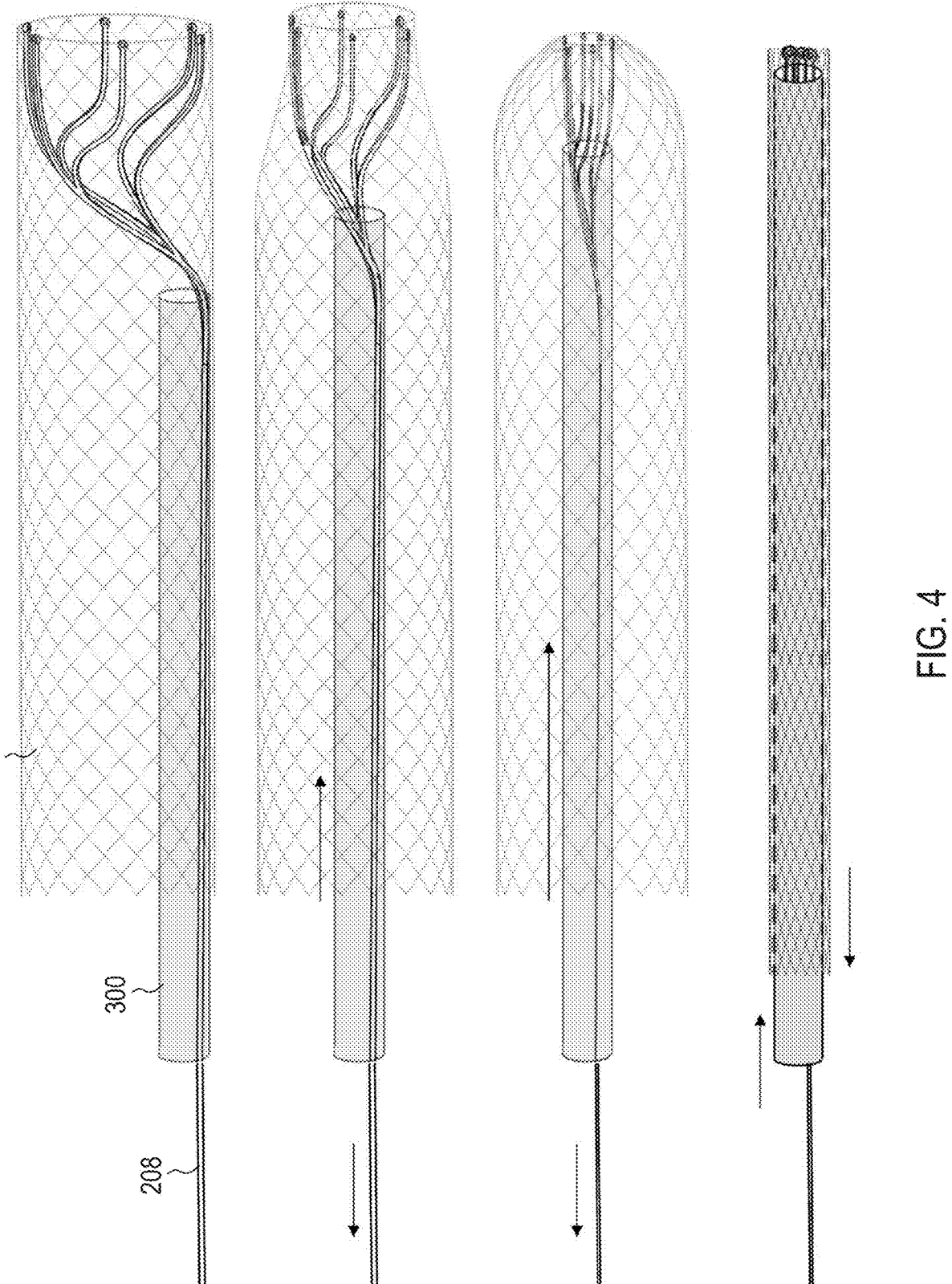
FIG. 4 shows exemplary steps for self-collapsing a braided section of an exemplary elongated tube using the actuator tube and actuation wire system.

FIG. 4 shows the steps of FIG. 3 in an exemplary embodiment where the collapsible section of the elongated tube is braided. Actuator tube 300 and actuation wire 208 may maintain elongated tube 200 in the collapsed state during delivery and, as illustrated in FIG. 4, also cause elongated tube 200 to transition from the expanded state to the collapsed state, for example, after removal of the obstruction from the blood vessel such that the catheter is removable from a subject in the collapsed state. As actuator tube 300 (e.g., a microcatheter) is advanced relative to the nitinol wire, this causes the self-collapse mechanism (e.g., the distal region of actuation wire 208) to be drawn into the microcatheter lumen. This causes the distal multi-armed structure to collapse radially inwards. When the self-collapse mechanism is fully withdrawn into microcatheter lumen, the distal tip of the braid is fully collapsed and the microcatheter is effectively attached to the distal end of the braid. By advancing the microcatheter even further, the braid is elongated and the entire braided structure can be collapsed onto the microcatheter, as shown at the bottom of FIG. 4.

Methods of using catheter system 100 are also provided herein. As should be understood, descriptions of the methods are for illustration only, the order of steps may be modified, and the steps are optional unless explicitly stated as mandatory.

Figure 5A:
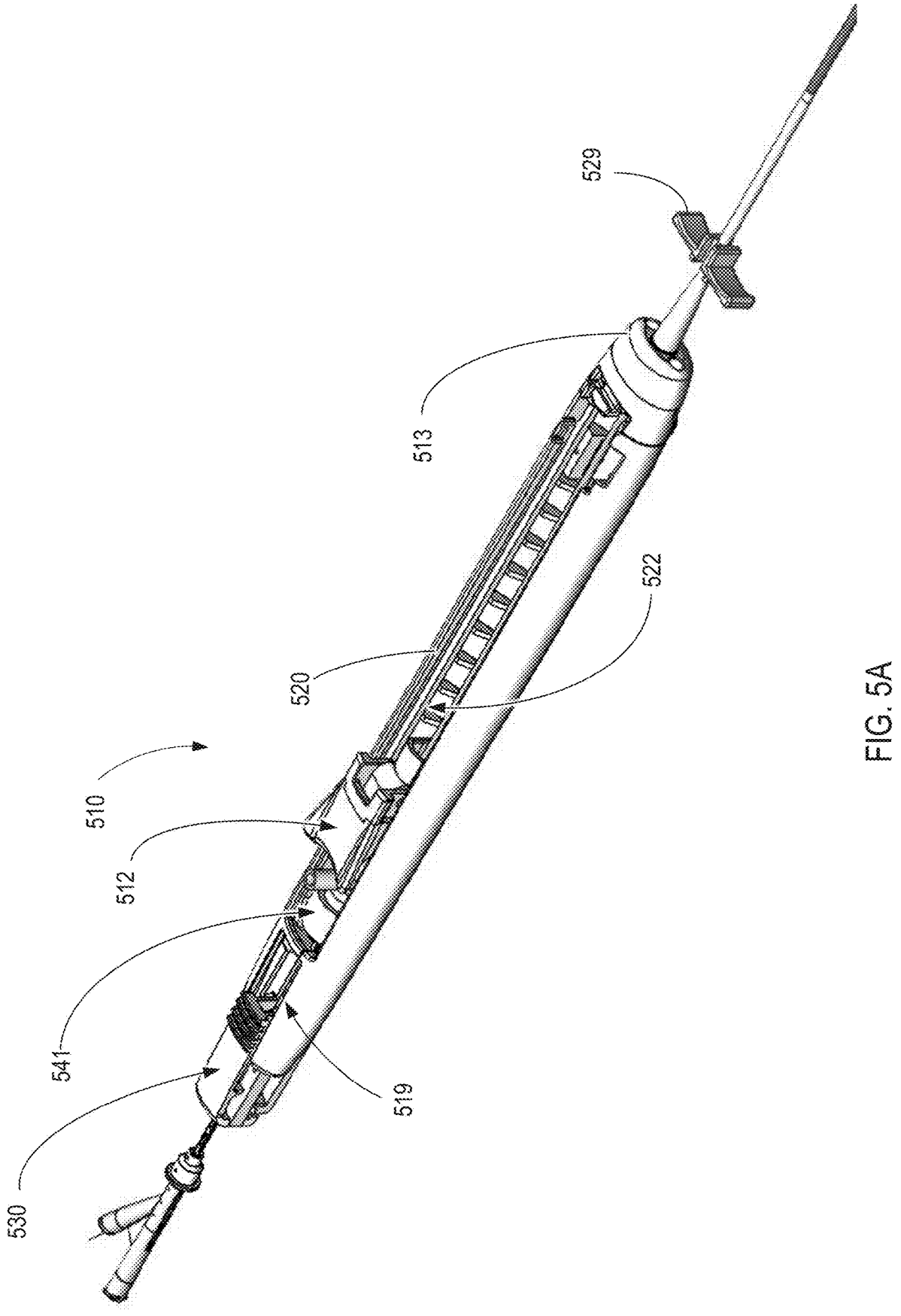
FIGS. 5A-5C illustrates a perspective and overhead views of a handle for controlling the actuator tube and intermediate tube of the catheter system.

Referring now to FIG. 5A, a perspective view of handle 510 is illustrated. Handle 510 may be the same as or similar to handle 110 of catheter system 100 illustrated in FIG. 1A and/or handle 610 in FIGS. 6A-6H. Handle 510 may include handle body 520 which be formed into an elongated tubular shape easily grasped by a user. Handle 510 may include a proximal portion (e.g., handle body 520) and a distal portion (e.g., distal end 513). Handle body 520 may include and/or define or at least partially define channel 522 which may be a void extending along a portion of handle body 520 which may include one or more rails, grooves, or other slidable structures. Actuator 512 may be positioned at least partially within and/or may interface with channel 522, including the rails, grooves, or other slidable structure such that actuator 512 may slide along or within channel 522.

Actuator 512 may be connected to the intermediate tube of the catheter system (e.g., intermediate tube 400 of FIG.

1A). Actuator 512 may be connected either directly or via a connection with the middle shaft to hemostasis valve 541, which may be the same as or similar to hemostasis valve 411 of FIG. 1A. Handle 510 may include distal end 513, which may be a distal end or distal portion of handle 510. Handle body 520 may connect to or otherwise incorporate the elongated tube and/or a hemostasis valve (e.g., via actuator 512) connected to the intermediate tube, which may be the same as or similar to elongated tube 200 and/or hemostasis valve 211 of FIG. 1A, respectively. In one example, hemostasis valve 541 may be coupled to actuator 512 and may be in fluid communication with the intermediate tube, which also may be coupled to actuator 512. Actuator 512 may be rotated upward with respect to handle body 520 to release actuator 512 and distal end 513 from handle body 520, thereby releasing the intermediate shaft and the elongated tube from the handle body, as shown in more detail in FIG. 6H. For example, actuator 512 may be a tab or other suitable structure that may be rotated at one end to transition from an unlocked position to a locked position.

Handle 510 may further include actuator 530 which may be connected to handle body 520 and may be selectively disconnected from handle body 520. For example, actuator 530 may include a snap or click engagement with handle body 520 and/or actuator 512 and may interface with and move along channel 519 defined at least partially by handle body 520. Actuator 530 may be released from handle body 520 when an end (distal end) of actuator 530 is compressed and pulled proximally, which may result in unlocking actuator 512 such that actuator 512 is free to move in channel 522. In this manner, actuator 530 may be inserted into and removed from channel 519. Actuator 530 may be connected to an actuator tube, such as actuator tube 300 of FIG. 1A, which may include a hemostasis valve (e.g., hemostasis valve 311). By actuating actuator 530, (e.g., compressing actuator 530), actuator 530 may be moved proximally with respect to handle body 520. Further actuator 530 may be fully disconnected from handle body, along with the actuator tube, by continuing to move actuator 530 proximally. Grip 529 may be positioned onto the elongated tube or other structure of handle 510 and may serve as a grip to aid manipulation of handle 510 (e.g., distal end 513 of handle 510). For example, a user may manipulate distal end 513 using grip 529 and/or actuator 512 (e.g., when actuator 512 is rotated into an upward and/or locked position).

Figures 5B, 5C:
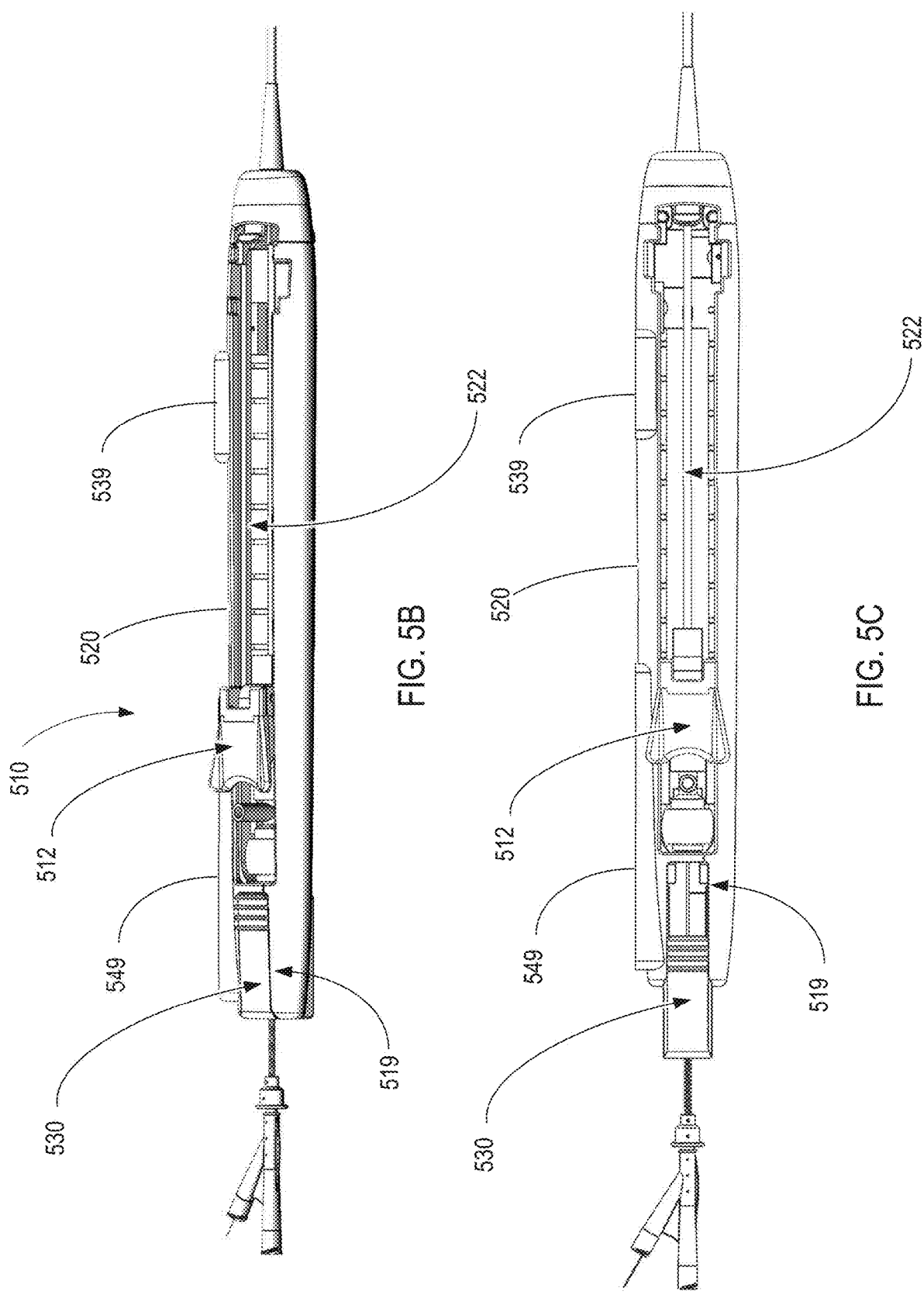

Referring now to FIG. 5B-5C, perspective and overhead views of handle 510 are illustrated. Handle 510 may optionally include surface 539 and/or surface 549. Surface 539 may be positioned on handle 510 adjacent to channel 522. Surface 549 may be positioned on handle body 520 adjacent to both channel 519 and channel 522. As show in FIGS. 5B-5C, surface 539 and/or surface 549 may be formed into, may be coupled to, and/or may extend from handle 510. Surface 539 and surface/or 549 may include a flat surface or a generally flat surface. The shape of surface 539 and/or surface 540 may be desirable in that handle 510 may rest on a flat surface without moving or changing position as surface 539 and/or surface 540 prevent rolling and/or rocking of handle 510 on the flat surface. In this manner, handle 510 may rest on a flat surface stably while actuators 530 and/or 512 are manipulated and/or actuated. Further, the shape of surface 539 and/or surface 540 may be desirable for ergonomic purposes and case of use by a healthcare provider. While both surface 539 and surface 549 are illustrated in FIGS. 5B and 5C, it may be desirable to include only surface 539 or surface 549 or to have more than two surfaces that resist movement when handle 510 is resting on a flat surface.

Referring now to FIGS. 6A-6H, a sequence and method are illustrated for guiding catheter system 110 to a distal site in the patient's vasculature and transitioning the distal end of the elongated tube to the expanded state. In FIGS. 6A-6H, handle 610 may be the same as or similar to handle 510 of FIG. 5A. For example, handle body 620, actuator 612, channel 622, and actuator 630 may be the same as or similar to handle body 520, actuator 512, channel 522, and actuator 530 of FIG. 5A, respectively. Further elongated tube 652, actuator tube 653, and intermediate tube 654 may be the same as or similar to elongated tube 200, actuator tube 300, and intermediate tube 400 of FIG. 1A.

Figure 6A:
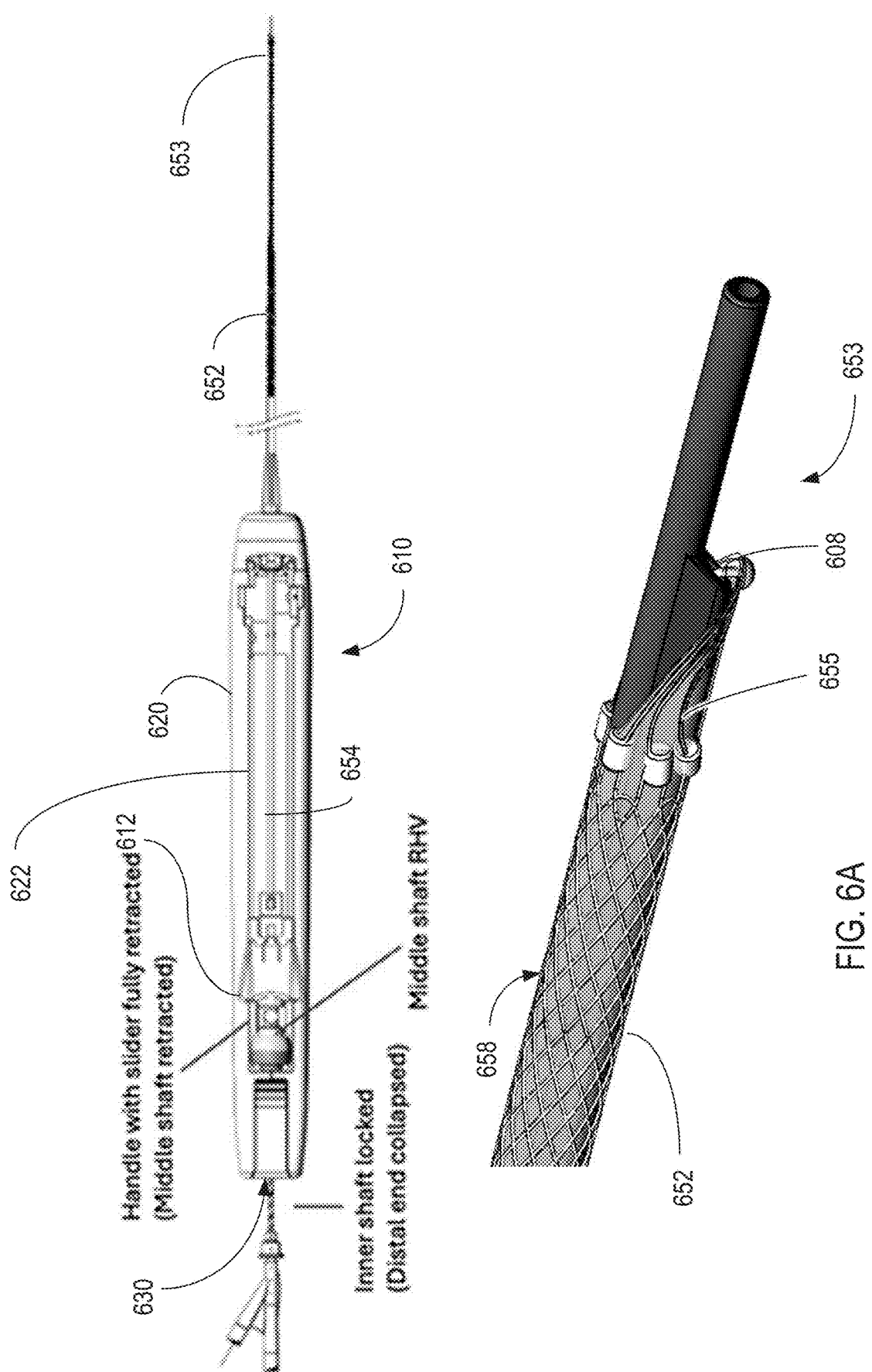

As shown in FIG. 6A, catheter system 600 may be transitioned to a collapsed state for navigating the vasculature with actuator tube 653 advanced in its distal most position with respect to elongated tube 652 using handle 610. In this configuration, actuator tube (e.g., inner shaft or inner tube) may be locked in its distal most position via actuator 630, causing the distal end of actuator tube 653 to engage a distal end of actuation wire 608 and move actuation wire 608 distally, thereby elongating and/or collapsing connection structure 655 and causing braided section 658 of elongated tube 652 to both extend and contract. In this position, actuator 612 may be maintained in a proximal most position such that intermediate tube 654 is not advanced toward the distal end of catheter system 600. Actuation wire 608, connection structure 655, elongated tube 652 and actuator tube 653 may be the same as actuation wire 1008, connection structure 1050, elongated tube 1002, and actuator tube 1030 of FIGS. 10A-10G. Braided section 658 and connection structure 655 may be coated with an expandable, lubricious coating as described in U.S. Patent Application Pub. No. 2025/0025192 to Behan, the entire contents of which are incorporated herein by reference.

Figure 6B:
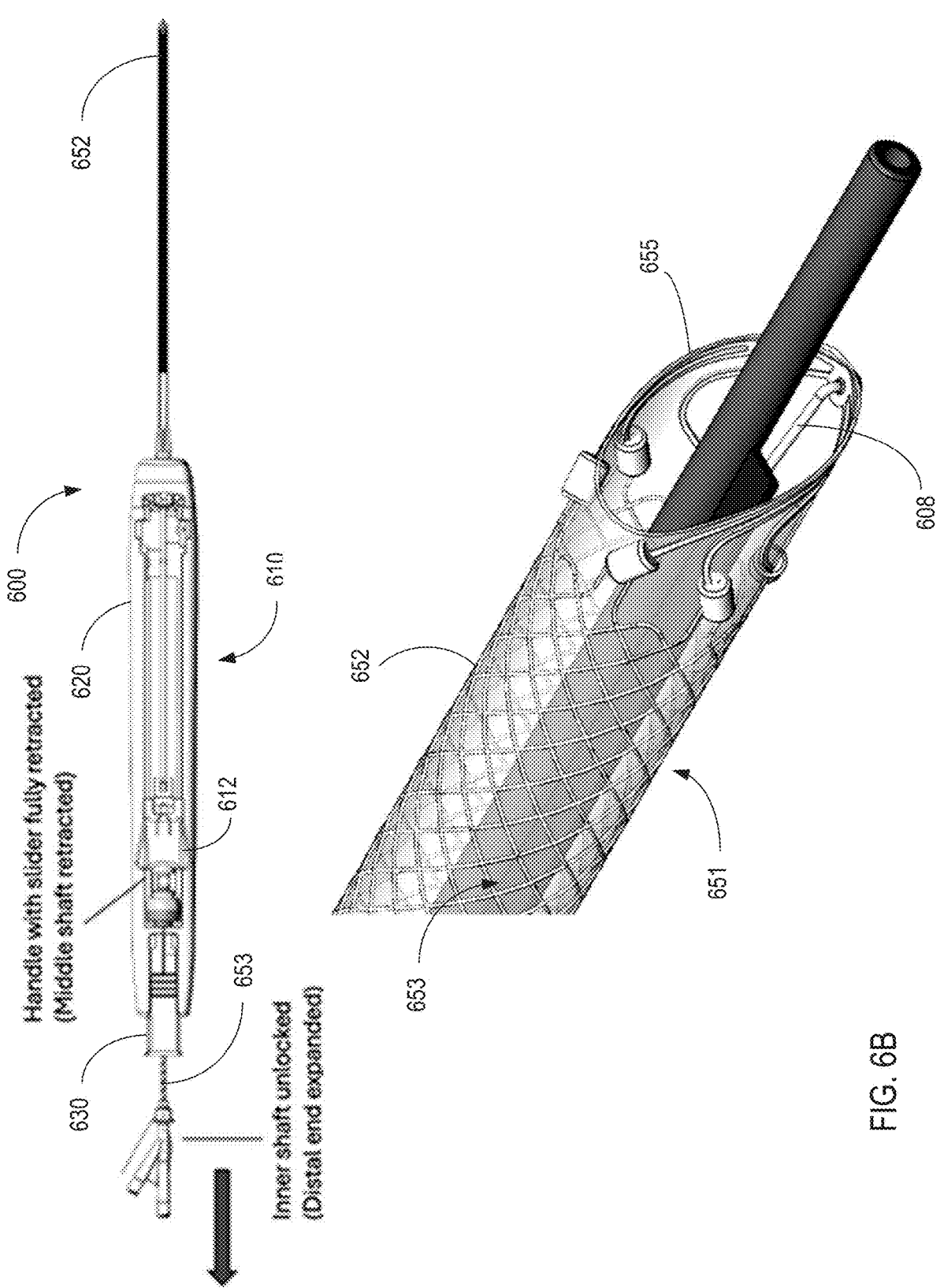

Referring now to FIG. 6B, catheter system 600 may be transitioned to an expanded state by retracting actuator 630 proximally using handle 610. Actuator 630 may be unlocked form handle body 620 (e.g., by compressing actuator 630 to unlock a clicking or snapping engagement) and may slide within and/or along handle body 620 as actuator 630 moves proximally. As actuator 630 moves proximally, so too will actuator tube 653 because actuator tube 653 is fixedly connected to actuator 630. As actuator tube 653 moves proximally, a distal end of actuation wire 608 will no longer interface with actuator tube 653 and thus connection structure 655 and braided section 651 may be permitted to expand. Connection structure 655 may be biased to expand outwardly.

As shown in FIG. 6B, actuator 630 may be retracted proximally, while still engaged with and interfacing with handle body 620, using handle 610. Alternatively, actuator 630 may be moved with respect to handle body 620 (e.g., actuator 630 may be moved proximally and/or handle body 620 may be moved distally). In one example, the user may compress actuator 630 and move handle body 620 distally. Handle body may have grooves, rails, or other slidable structure that actuator 630 may engage with to slide along handle body 620. Braided section 651 and/or connection structure 655 may be biased to expand outward and when actuation wire 608 is released from engagement with actuator tube 653, braided section 651 may self-expand outward as there is no contracting force being applied to braided section 651.

In one example, actuator 630 may engage actuator 612 and may lock actuator 612 in the proximal-most position when actuator 630 is in its distal-most position. In the locked positioned, neither actuator 630 nor actuator 612 may move with respect to one another or handle body 620. In this manner, actuator 630 may be locked to handle body 620 via its engagement with actuator 612 and actuator 612 may be locked to handle body 620 via its engagement with actuator 630. When actuator 630 is unlocked from actuator 612, actuator 630 may be permitted to move proximally and actuator 612 may be permitted to move distally. Actuator 630 and actuator 612 may be connected to one another via any suitable snap or click engagement, for example, and/or may be released (e.g., unlocked) via deflection or compression of a portion of actuator 630 and/or actuator 612.

Figure 6C:
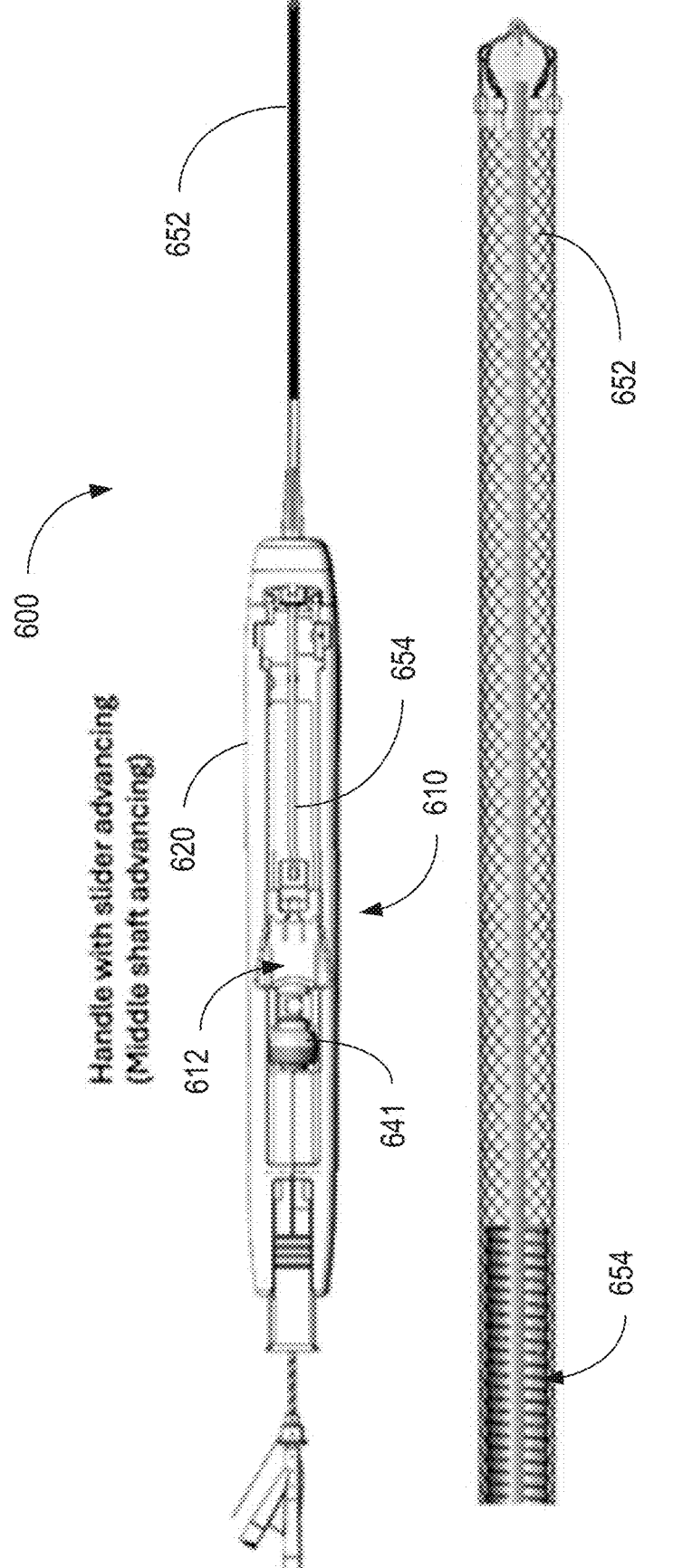

Referring now to FIG. 6C, intermediate tube 654 (e.g., middle shaft) may be advanced distally within elongated tube 652 using actuator 612 of handle 610. As shown in FIG. 654, intermediate tube 654 may be hypotube made from biocompatible metal such as nitinol or stainless steel. For example, intermediate tube 654 may be a laser cut hypotube such as the hypotube illustrated in FIG. 9. In another example, intermediate tube 654 may be a tightly wound coil such that adjacent turns in the coil contact one another. Intermediate tube 654 may permit insertion of additional interventional devices (e.g., actuator tube 300) into a lumen of intermediate tube 654 (e.g., via hemostasis valve 641, which may be the same as hemostasis valve 641 of FIG. 6C). In one example, intermediate tube 654 may connect to a vacuum source (e.g., via hemostasis valve 641 or other connector) for aspiration of the obstruction in the blood vessel. Alternatively, intermediate tube 654 may connect (e.g., via hemostasis valve 641 or other connector) to any suitable treatment instrument or device for delivering treatment to the target site via intermediate tube 654.

Figure 6D:
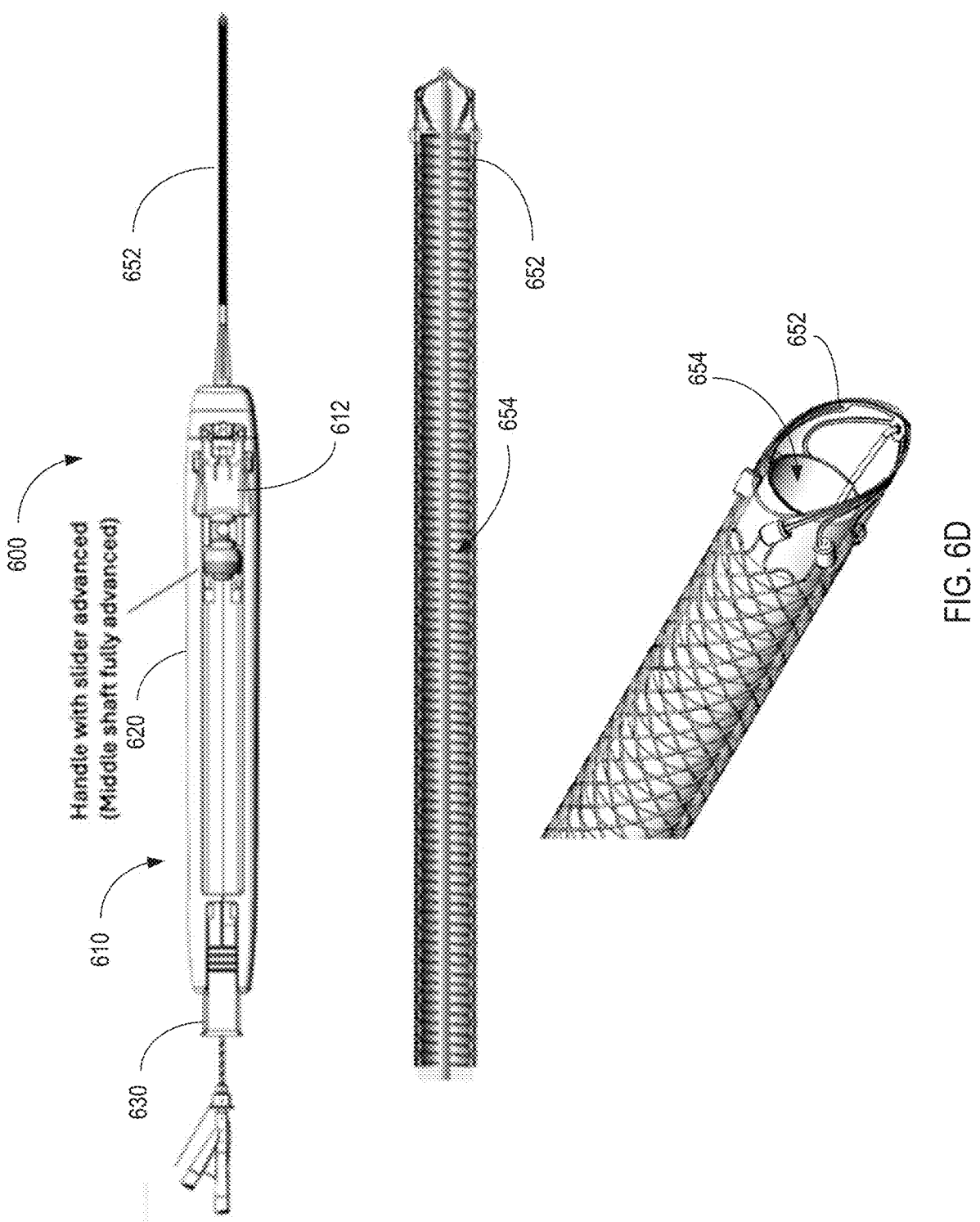

Referring now to FIG. 6D, intermediate tube 654 may be extended distally to the distal end of elongated tube 652 using actuator 612 of handle 610. For example, actuator 612 may be advanced toward the distal end of handle body 620 to cause intermediate tube 654 to move distally. As shown in FIG. 6D, actuator 630 may be maintained in the proximally retracted positioned yet still engaged with handle body 620 while actuator 612 is advanced distally along handle body 620.

Figure 6E:
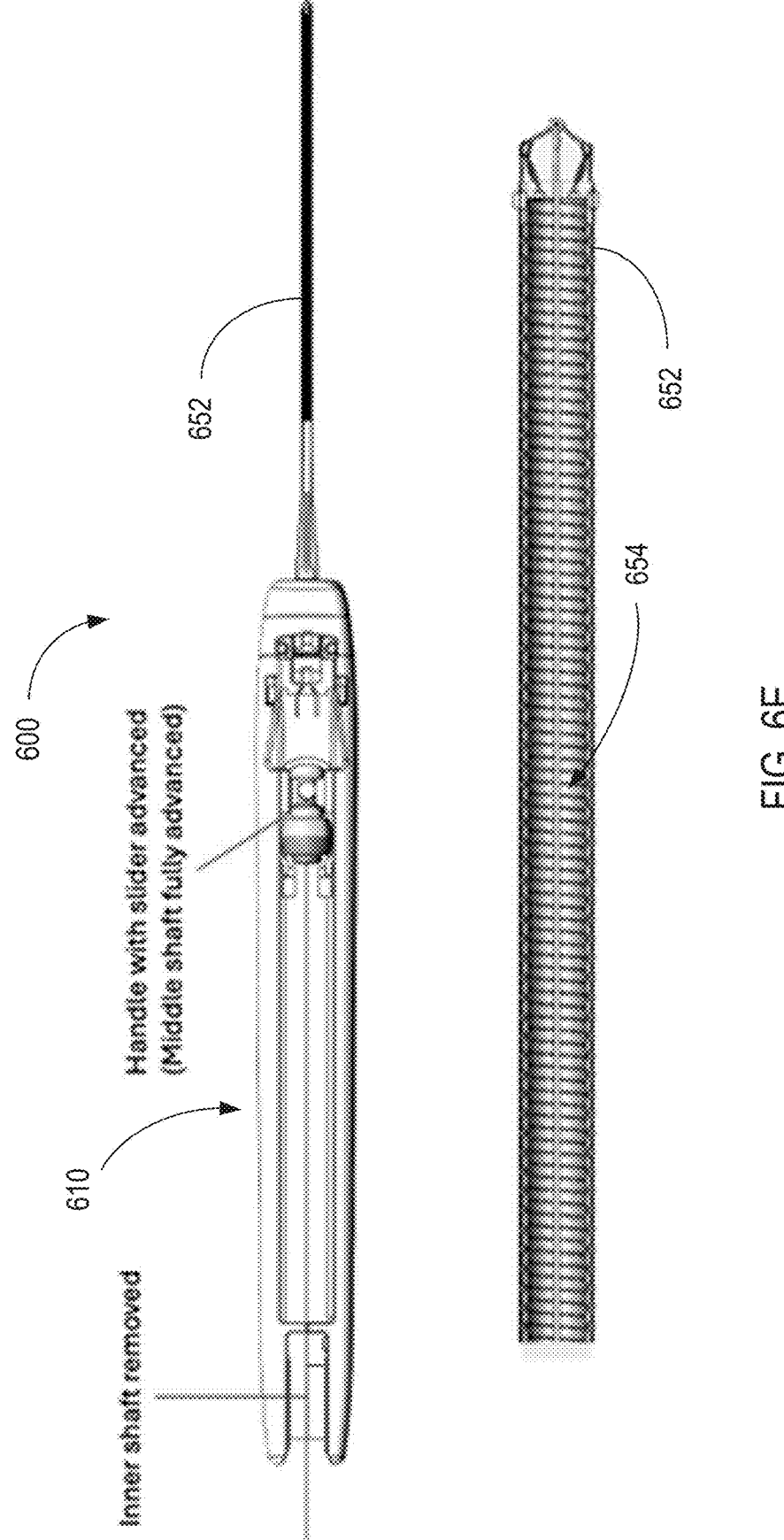

Referring now to FIG. 6E, actuator 630 (not shown) may be fully removed from handle 610 of catheter system 600 after intermediate tube 654 is fully distally extended. For example, actuator 630 (not shown) may be further advanced proximally from its position in FIG. 6D.

Referring now to FIGS. 6F-6H the process for disengaging handle body 620 from distal end 613 is illustrated. It may be desirable to remove handle body 620 from distal end 613 to permit easy access to hemostasis valve 641 connected to intermediate tube 654, for example. To disengage handle body 620 from distal end 613 and actuator 612, which may be coupled to elongated tube 652 and intermediate tube 654, respectively, actuator 612 may be rotated upward, as shown in FIG. 6F. Rotating actuator 612 may cause a snapping or clicking engagement feature, or other suitable locking feature, to unlock distal end 613 from handle body 620. For example, FIG. 6G shows distal end 613 and actuator 612 disconnecting from handle body 620 and FIG. 6H shows distal end 613 and actuator 612 entirely disconnected from handle body 620, while elongated tube 652 and intermediate tube 654 remain connected to distal end 613 and/or actuator 612. While distal end 613 and actuator 612 are locked to one another, elongated tube 652 and intermediate tube 654 are prevented from moving axially with respect to one another.

With distal end 613 and actuator 612 disconnected from handle body 620, and with actuator tube 653 (not shown) fully retracted proximally from intermediate tube 654 and elongated tube 652, the interior lumen of intermediate tube 654 may be easily accessible by a user (e.g., via hemostasis valve 641). For example, additional interventional devices may be inserted into a lumen intermediate tube 654 and/or intermediate tube 654 may be connected to a vacuum source for aspiration.

FIGS. 6I and 6H illustrate distal end 613 and actuator 612 entirely disconnected from a proximal portion of the handle, while the elongated tube and intermediate tube, as well as hemostasis valve 641 connected to intermediate tube, remain connected to distal end 613 and/or actuator 612. As shown in FIG. 6H, grip 629 may be secured distal to distal end 613 or structure adjacent to distal end 613. Grip 629 may be the same as grip 529 of FIG. 5A.

Referring now to FIGS. 7A through 7F, an exemplary method for removing an obstruction from a blood vessel using catheter system 701 is illustrated. Catheter system 701 may be the same as or similar to catheter system 600, for example, or any other catheter system described herein. An obstruction within a blood vessel is identified using standard visualization techniques. For example, a patient experiencing ischemic stroke may be determined to have an obstruction O in the M1 segment of the middle cerebral artery MCA branching from the internal carotid artery ICA.

Figure 7B:
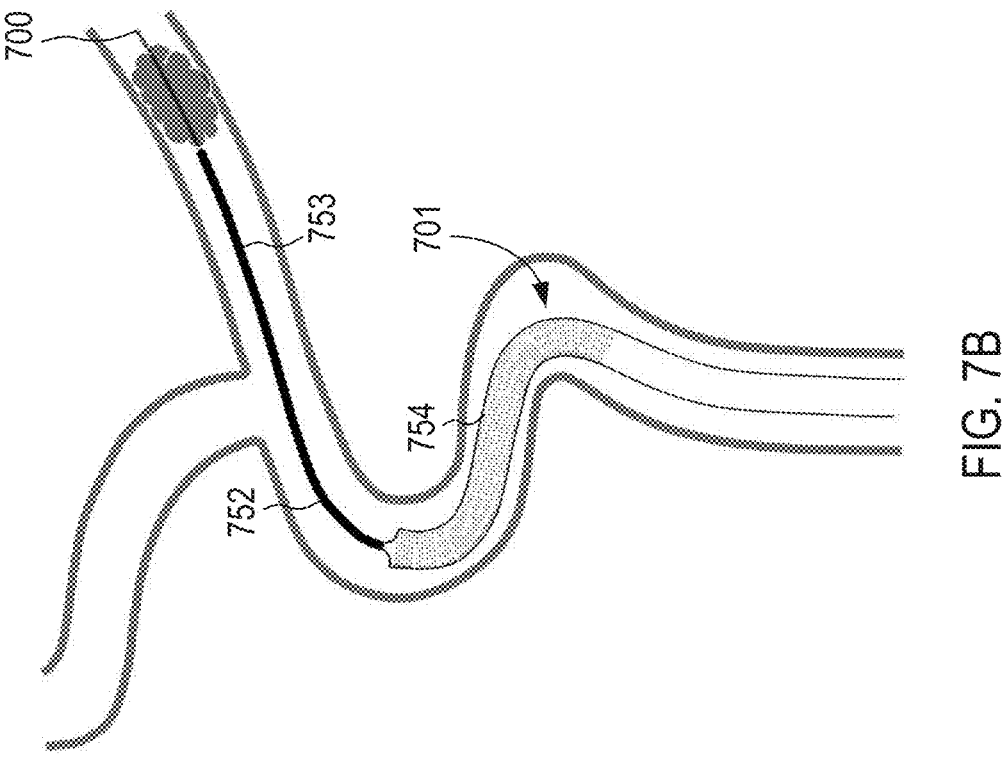
FIGS. 7A-7F illustrate an exemplary method for retrieving a clot in the vasculature using the catheter system.
Figure 7A:
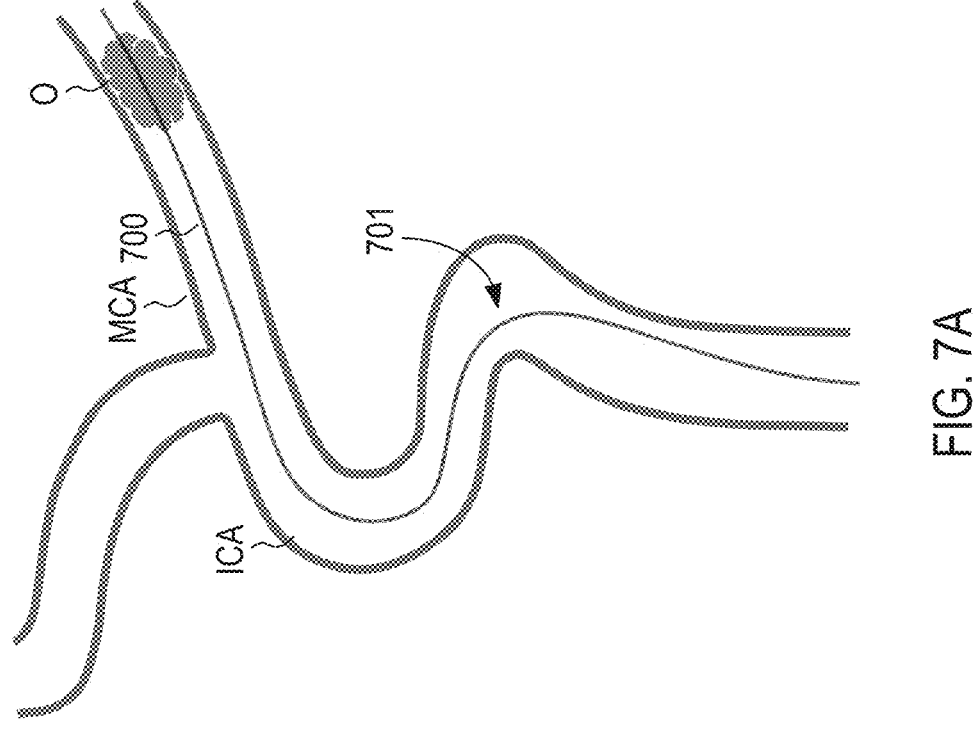

As shown in FIG. 7A, a clinician may navigate guidewire 700 to target obstruction O. The distal end of guidewire 700 may cross the obstruction O as illustrated. Next, as shown in FIG. 7B, catheter system 701 may be advanced over guidewire 700 until the distal tip of the catheter system 701 is positioned within at a desired location within the blood vessel, such as just proximal to the obstruction O. In some embodiments, guidewire 700 is advanced through the guidewire lumen in actuator tube 753 of catheter system 701 using a handle at the proximal end of the handle system (e.g., a handle that is the same or similar to handle 110 or handle 610). Actuator tube 753 may engage elongated tube 752 and may be positioned within intermediate tube 754. Actuator tube 753, elongated tube 752, and intermediate tube 754 may be the same as or similar to actuator tube 653, elongated tube 652, and intermediate tube 654, respectively.

Figure 7D:
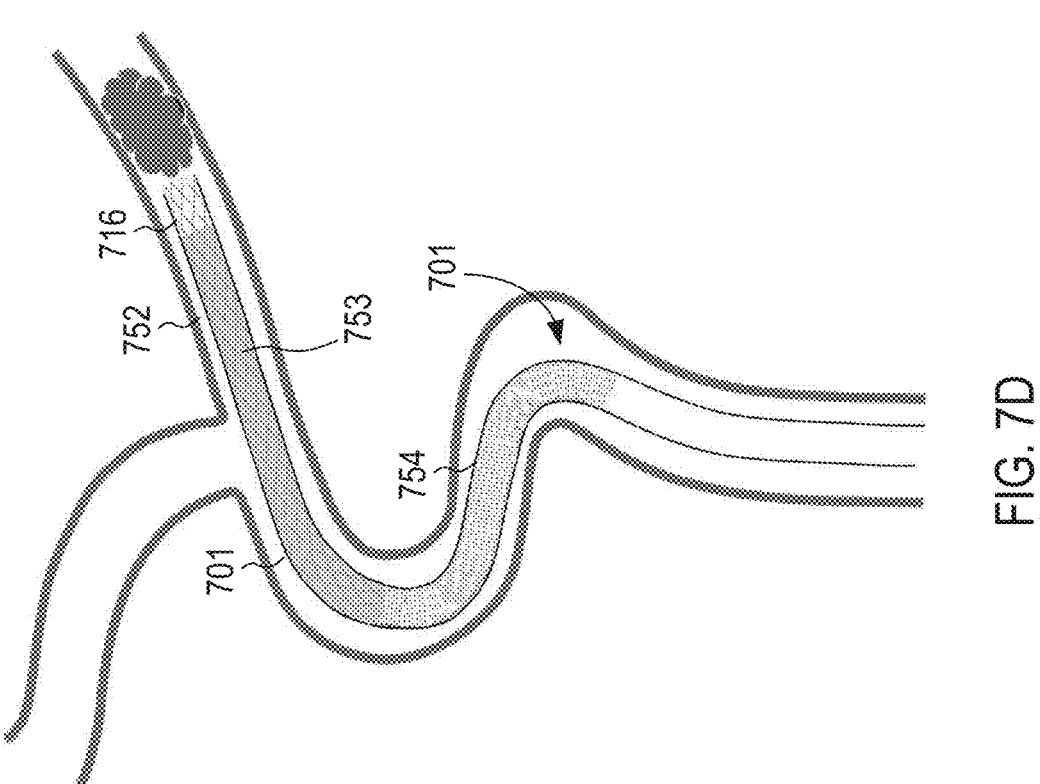
Figure 7C:
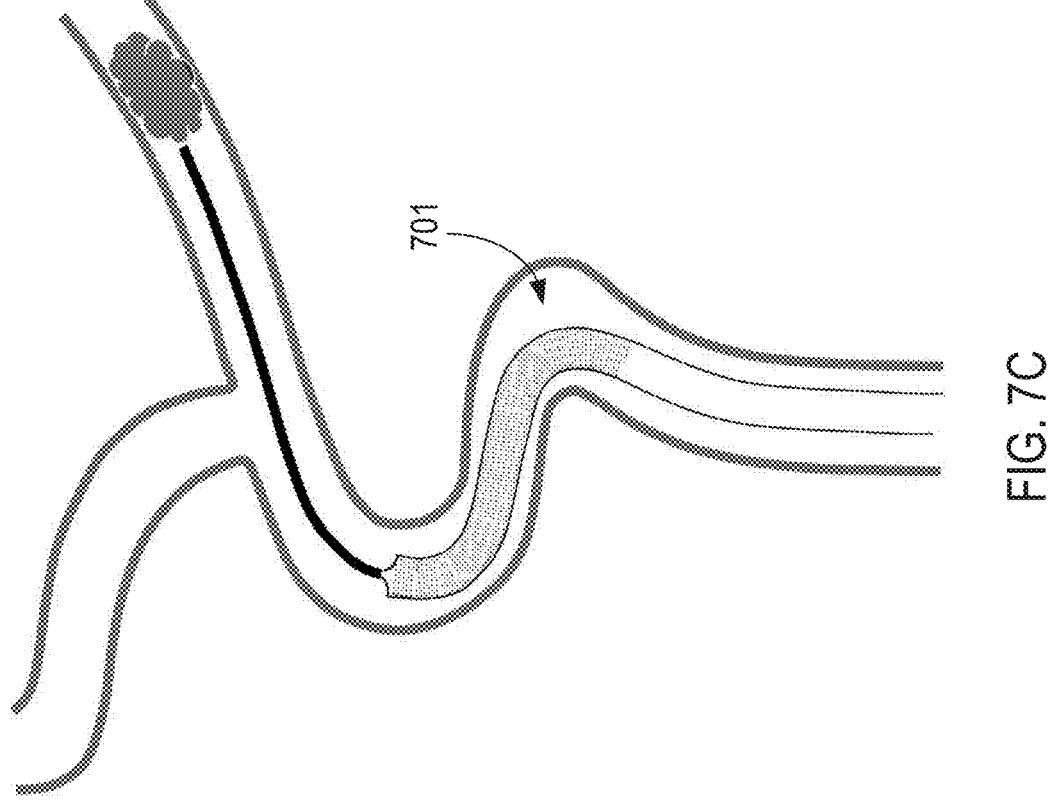

Then, the guidewire may be removed from catheter system 701, and thereby from the patient, as shown in FIG. 7C.

Then, as shown in FIG. 7D, while the clinician holds the distal tip of the catheter system 701 in place, actuator tube 753 is unlocked using the handle to permit actuator tube 300 to move proximally to expand distal braid 716 of elongated tube 752. For example, actuator tube 753 may be translated relative to the actuation wire (e.g., actuator tube 753 may be caused to move proximally relative to the actuation wire a to cause a plurality of struts of the connection structure coupled to the actuation wire to expand radially outward to transition elongated tube 752 to an expanded state within the blood vessel. In some embodiments, actuator tube 753 may be moved proximally relative to the actuation wire such that the expandable distal portion of the actuation wire expands, thereby causing the braid to expand. The actuator tube may then be removed from the patient.

Figure 7F:
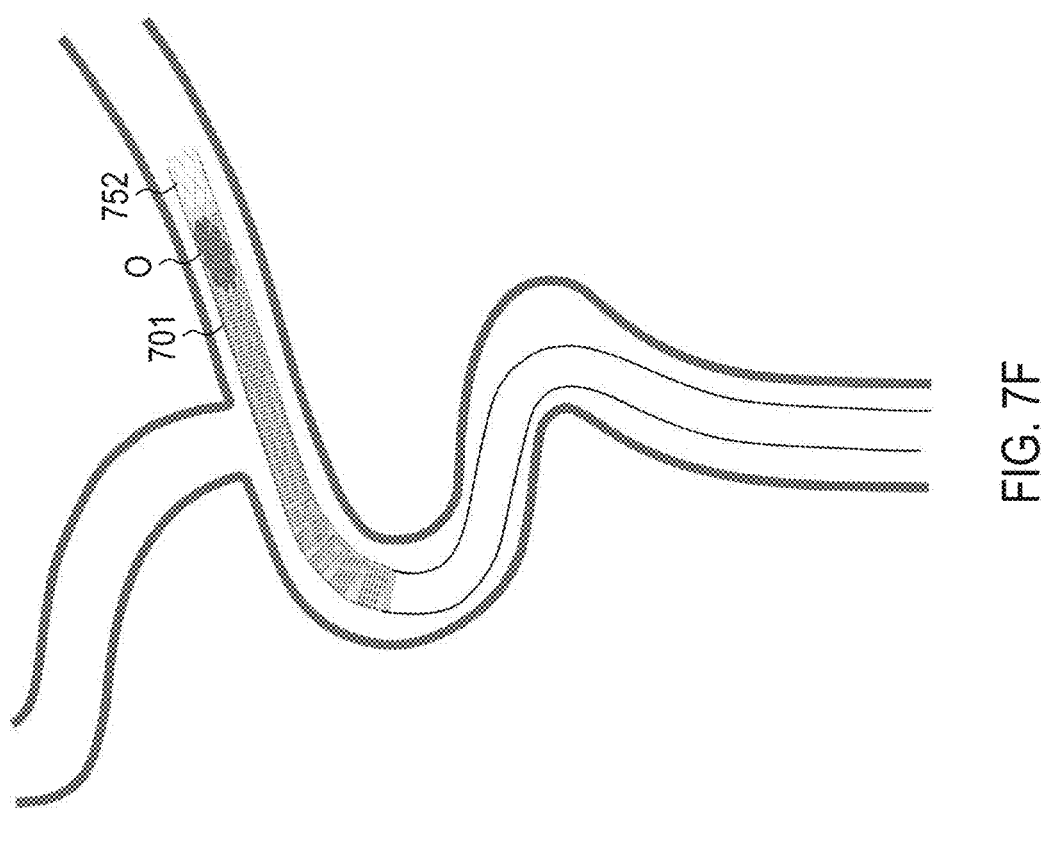
Figure 7E:
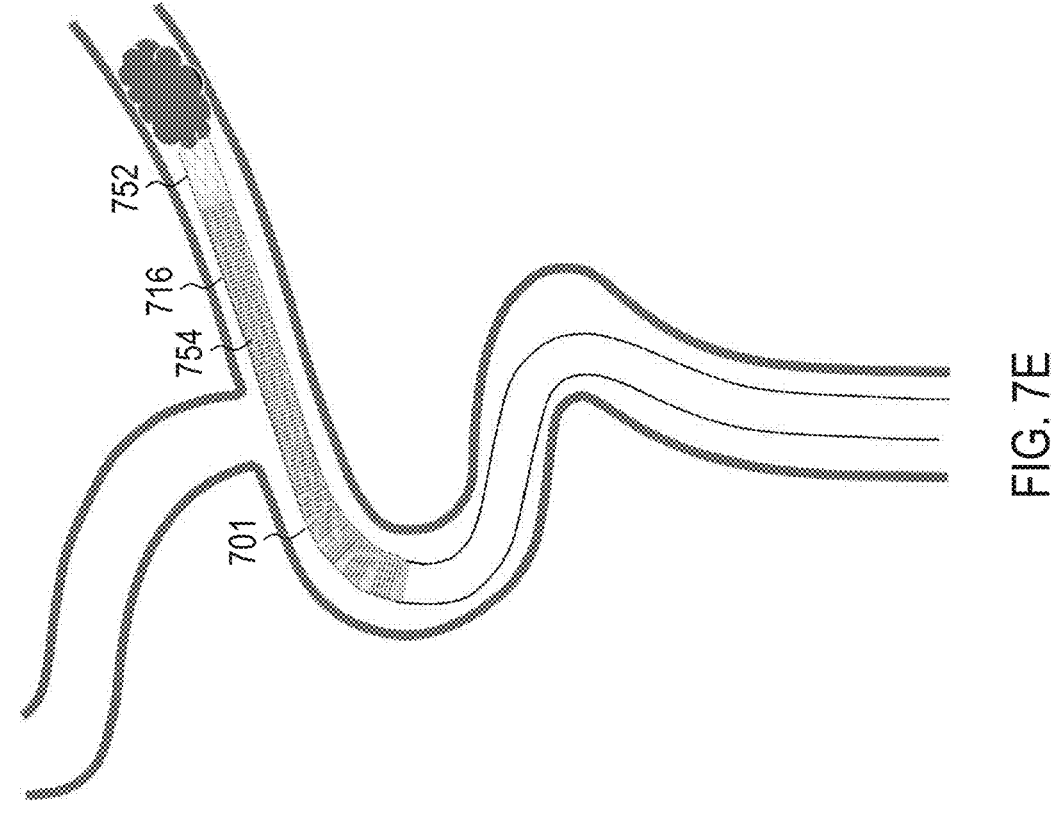
Figures 8A, 8B, 8C, 8D, 8E, 8F:
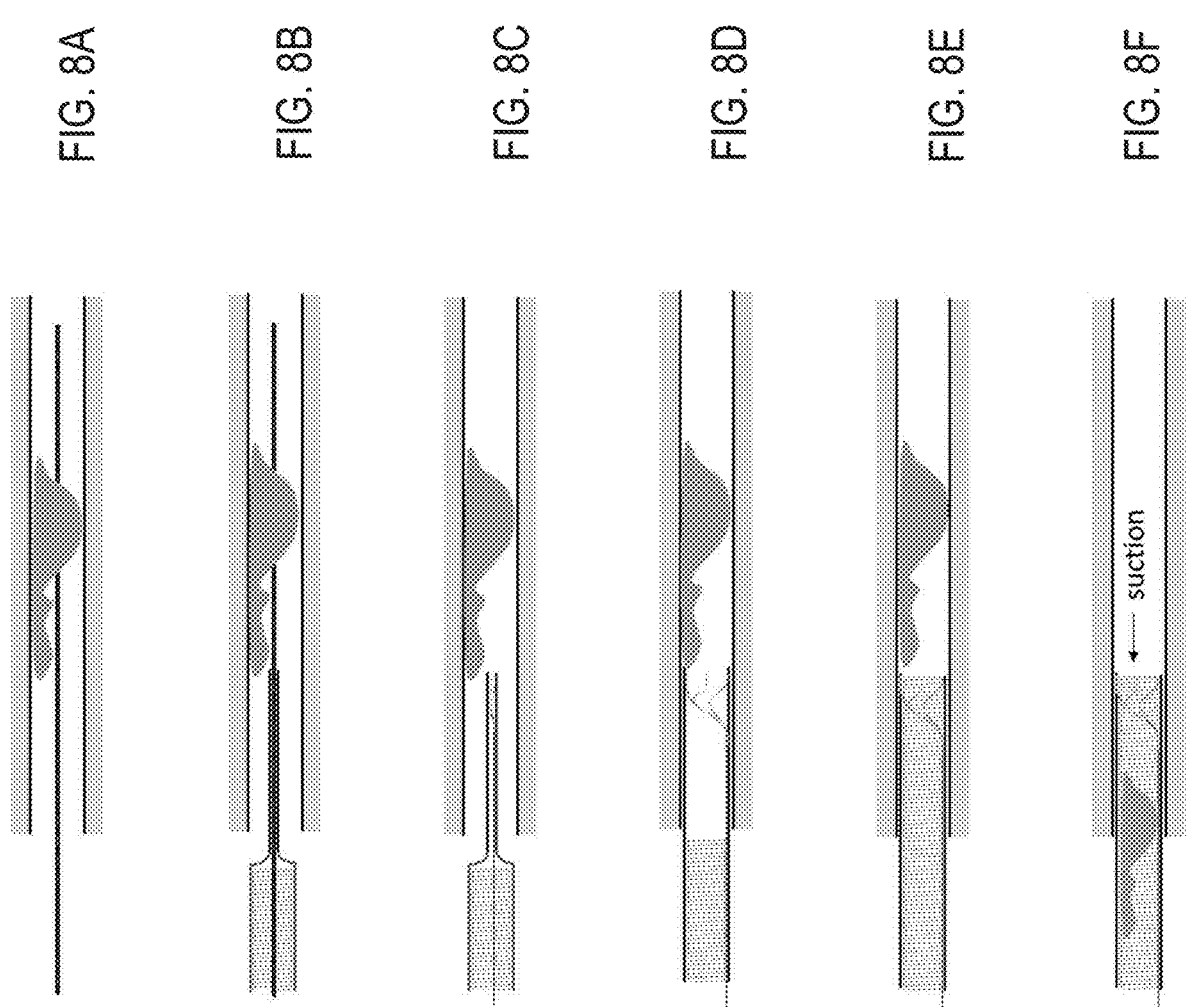
FIGS. 8A-8F show side views of the exemplary method in FIGS. 7A-7F for retrieving a clot in the vasculature using the catheter system.

Referring now to FIG. 7E, intermediate tube 754 is advanced distally relative to elongated tube 752 such that the distal portion of intermediate tube is disposed in distal braid 716 to reinforce the distal catheter shaft. Next, suction may be applied into the lumen of the catheter such that the obstruction is aspirated into the lumen of catheter system 701, as shown in FIG. 7F. Next, the catheter may be transitioned from the expanded state to the collapsed state (e.g., by once again extending the actuator tube distally) and elongated tube 752 may be removed from the patient or moved elsewhere in the collapsed state. For example, actuator tube 753 may be translated relative to the actuation wire to cause the plurality of struts of the connection structure connected to the actuation wire to collapse radially inward to transition elongated tube 752 to the collapsed state within the blood vessel for repositioning/removal.

FIGS. 8A through 8F show side views of the exemplary method of FIGS. 7A through 7F for further clarity.

Figure 9:
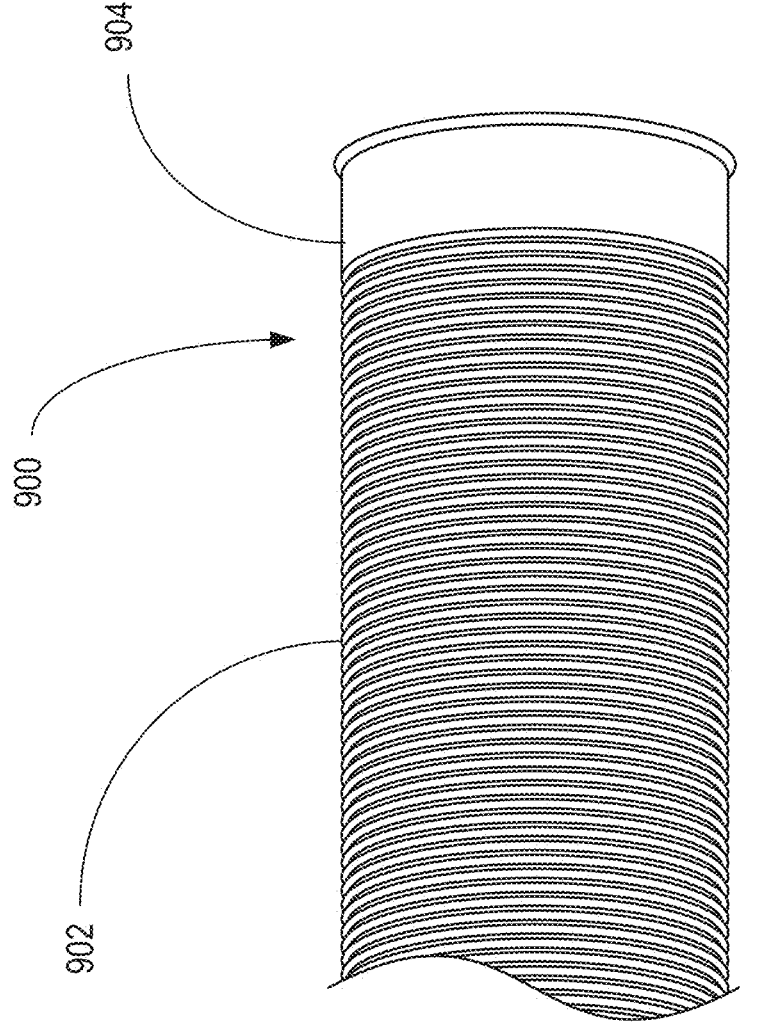
FIG. 9 illustrates a hypotube that may be positioned at the distal end of the intermediate tube of the catheter system.

Referring now to FIG. 9, a hypotube which may form a distal end of the intermediate tube is illustrated. For example, hypotube 900 may be a laser cut hypotube which may include a pattern of laser cuts 902 resulting in flexibility in hypotube 900 such that hypotube 900 may be positioned within elongated tube (e.g., elongated tube 652 of FIG. 6A) and advanced to a distal end of the elongated tube. Hypotube 900 may further include distal end 904 which may be a region with no laser cuts and thus may have a greater degree of rigidity than the rest of hypotube 900. It will be understood by one of ordinary skill in the art that hypotube 900 may be incorporated into or otherwise used together with the intermediate tube (e.g., hypotube 900 may be the distal end of tube 654 illustrated in FIG. 6E).

Figures 10A, 10B:
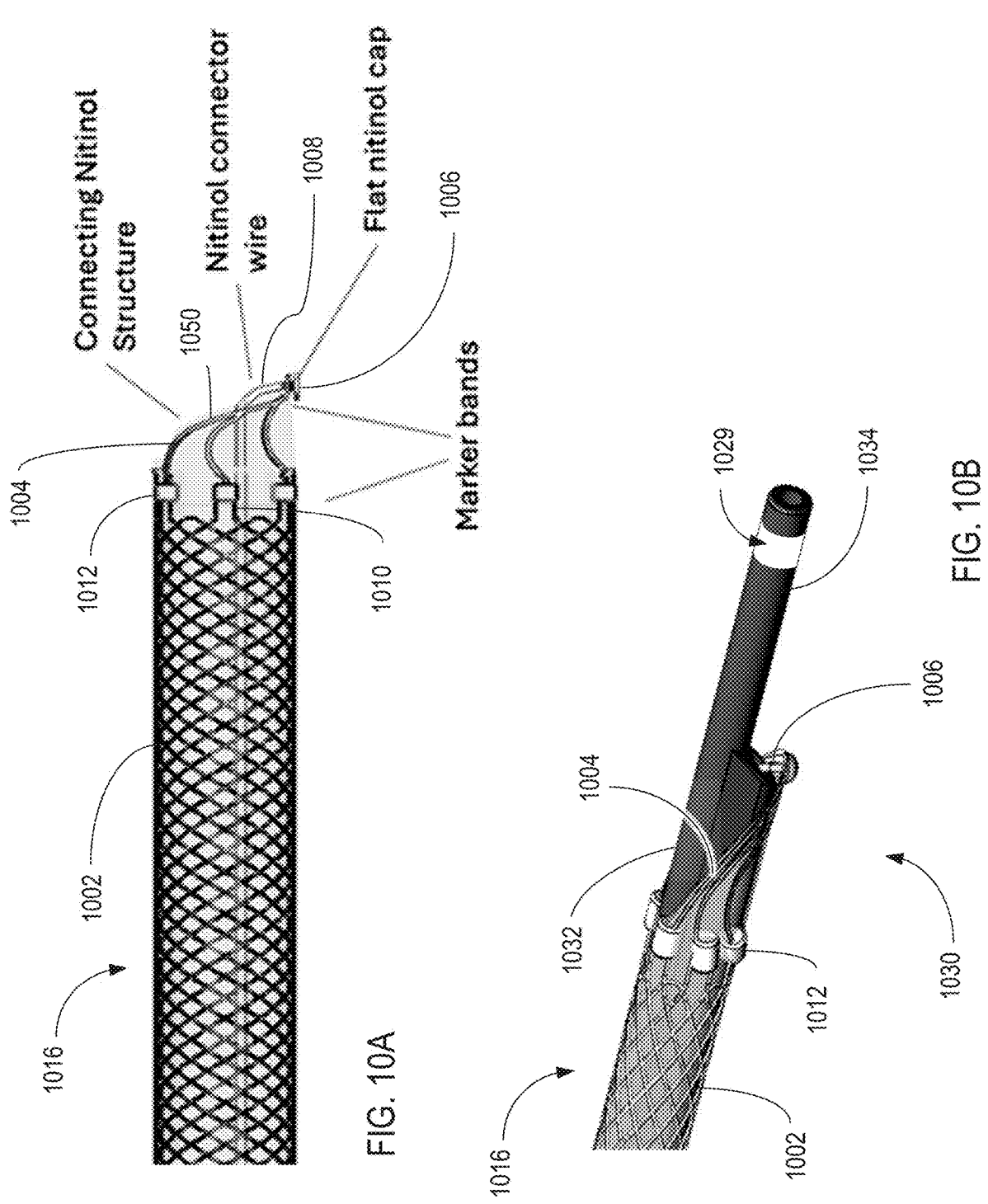
FIGS. 10A-10G illustrate an alternative actuation wire and connection structure for interfacing with the actuator tube and transitioning the elongated tube between the collapsed and the expanded states.

Referring now to FIGS. 10A-10G, an alternative connection structure connecting braided section of the elongated tube and to the actuation wire is illustrated. As shown in FIG. 10A, braided section 1016 of elongated tube 1002 is illustrated connected to actuation wire 1008 via connection structure 1050 including a plurality of struts 1004 biased to expand radially outward to transition elongated tube 1002 to the expanded state. Plurality of struts 1004 may connect to loops 1010 at the distal end of braided section 1016 via clips 1012. Braided section 1016 has a plurality of radiopaque markers disposed around the circumference of the braid, for example, at the distal end of the braid. Advantageously, radiopaque markers are spaced close together when the braid is collapsed (shown in FIG. 10B) such that the radiopaque markers appear as a solid line under visualization (e.g., fluoroscopy), but spaced apart when expanded (shown in FIG. 10A) such that the radiopaque markers appear spaced apart under visualization when expanded. As such, the radiopaque markers may be used to show when the braid is collapsed versus expanded. In some embodiments, clips 1012 are used as radiopaque markers. Actuation wire 1008 may include stopper 1006 that may interface with struts 1004. Stopper 1006 may be a flat cap, plate, ball, or any other suitable engagement structure. For example, struts 1004 may be formed into a disk shape at their distal end with a void through which actuation wire 1008 may extend. Actuation wire 1008 may terminate at cap 1006, which may too large to traverse the void, thereby securing actuation wire 1008 to connection structure 1050. The distal end of the actuation wire 1008 may include a radiopaque marker for visualizing the distal end. In some embodiments, cap 1006 is used as radiopaque marker.

As shown in FIG. 10B, braided section 1016 of elongated tube 1002 may be transitioned into a collapsed state by actuator tube 1030, which may be the same as or similar to actuator tube 653. Actuator tube 1030 may have dual lumens including guidewire lumen 1034, which may be designed to receive a guidewire, and actuation lumen 1032 which may be designed to receive actuation wire 1008. A radiopaque marker or other visualization marker may be included at the distal end of guidewire lumen 1034 for visualizing the distal end of the inner shaft. For example, marker 1029 may be positioned at the distal end of guidewire lumen 1034.

To collapse braided section 1016, actuator tube 1030 may be advanced distally until stopper 1006 interfaces with an end of lumen 1032. Stopper 1006 may be sized such that it is too large to enter lumen 1032. As a result, further advancement of actuator tube 1030 after stopper 1006 has contacted lumen 1032 will cause the plurality of struts 1004 and braided section 1016 to stretch and otherwise collapse inward, as shown in FIG. 10B. When braided section 1016 is collapsed inward, clips 1012 which connect braided section 1016 to the plurality of struts 1004 will appear to move closer to one another in imaging. For example, a user may use medical imaging to obverse clips transition between a close orientation corresponding to the collapsed state in FIG. 10B, which may appear as a band, to a spread apart orientation corresponding to the expanded state in FIG. 10A. Accordingly, a user may view clips 1012 via imaging to determine what state (e.g., collapsed or expanded) braided section 1016 is in.

Figures 10C, 10D:
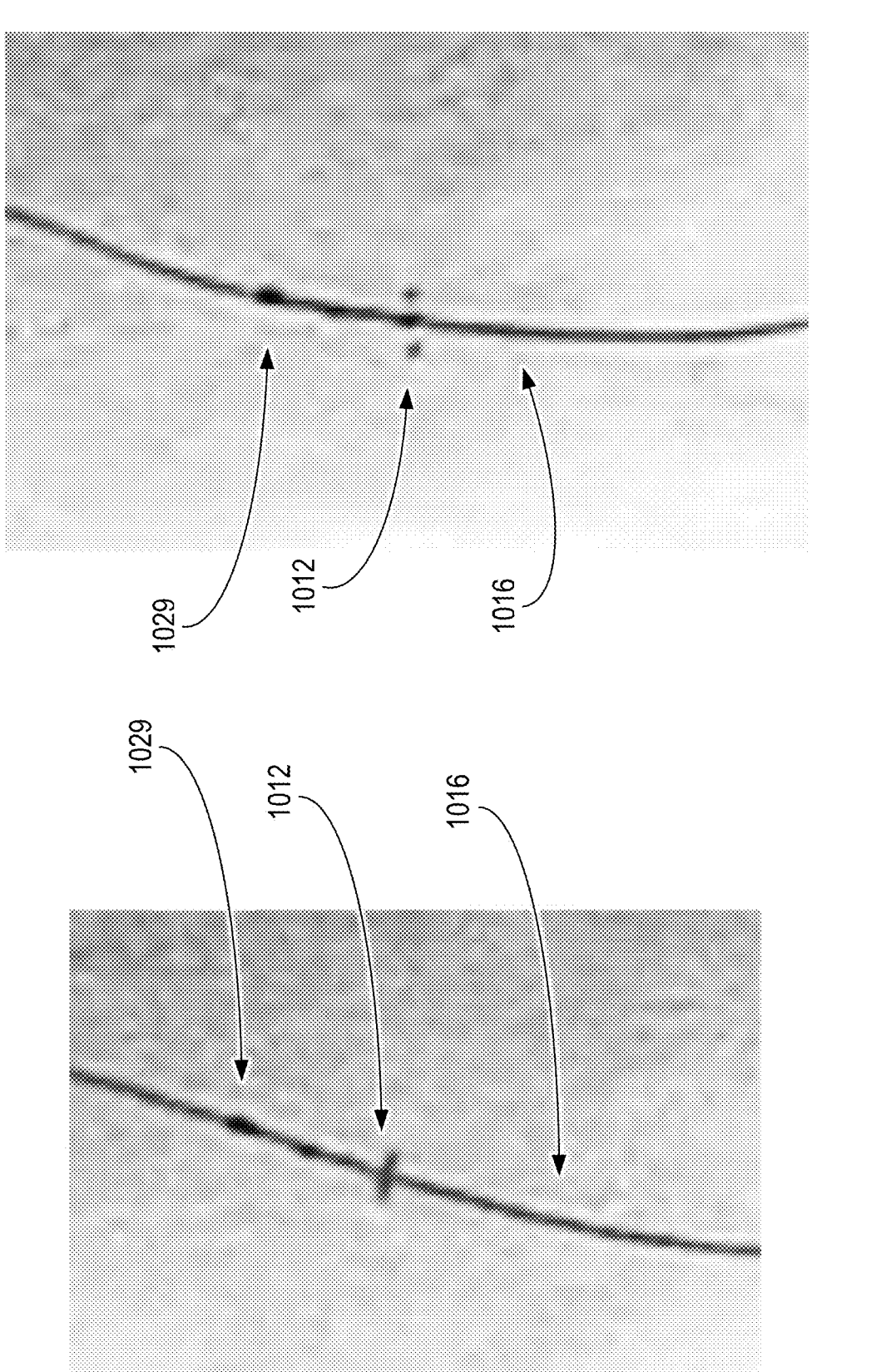

Referring now to FIGS. 10C-10D, exemplary fluoroscopy images of braided section 1016 in a collapsed and expanded state are illustrated. As shown in FIG. 10C, braided section 1016 is in the collapsed (e.g., contracted) state. As braided section 1016 is in the collapsed state, clips 1012 may appear in a fluoroscopy images or other medical images as a straight line due to each clip 1012 being positioned in close proximity to an adjacent clip 1012 when braided section 1016 is in the collapsed state. Marker 1029 is also illustrated in FIG. 10A, positioned distally to clips 1012. Referring now to FIG. 10B, braided section 1016 is in an expanded state. As braided section 1016 is in the expanded state, clips 1012 may appear in fluoroscopy images or other medical images as individual clips, blocks, or dots, indicating that braid section 1016 expanded to the expanded state, as each of clip 1012 moved apart from one another. Marker 1029 is also illustrated in FIG. 10B, positioned distally to clips 1012. In this manner, it may be clear under fluoroscopy imaging when braided section 1016 is in the collapsed state versus the expanded state. Clips 1012 may alternatively be any type of suitable marker that may visually appear in medical imaging.

Figures 10E, 10F:
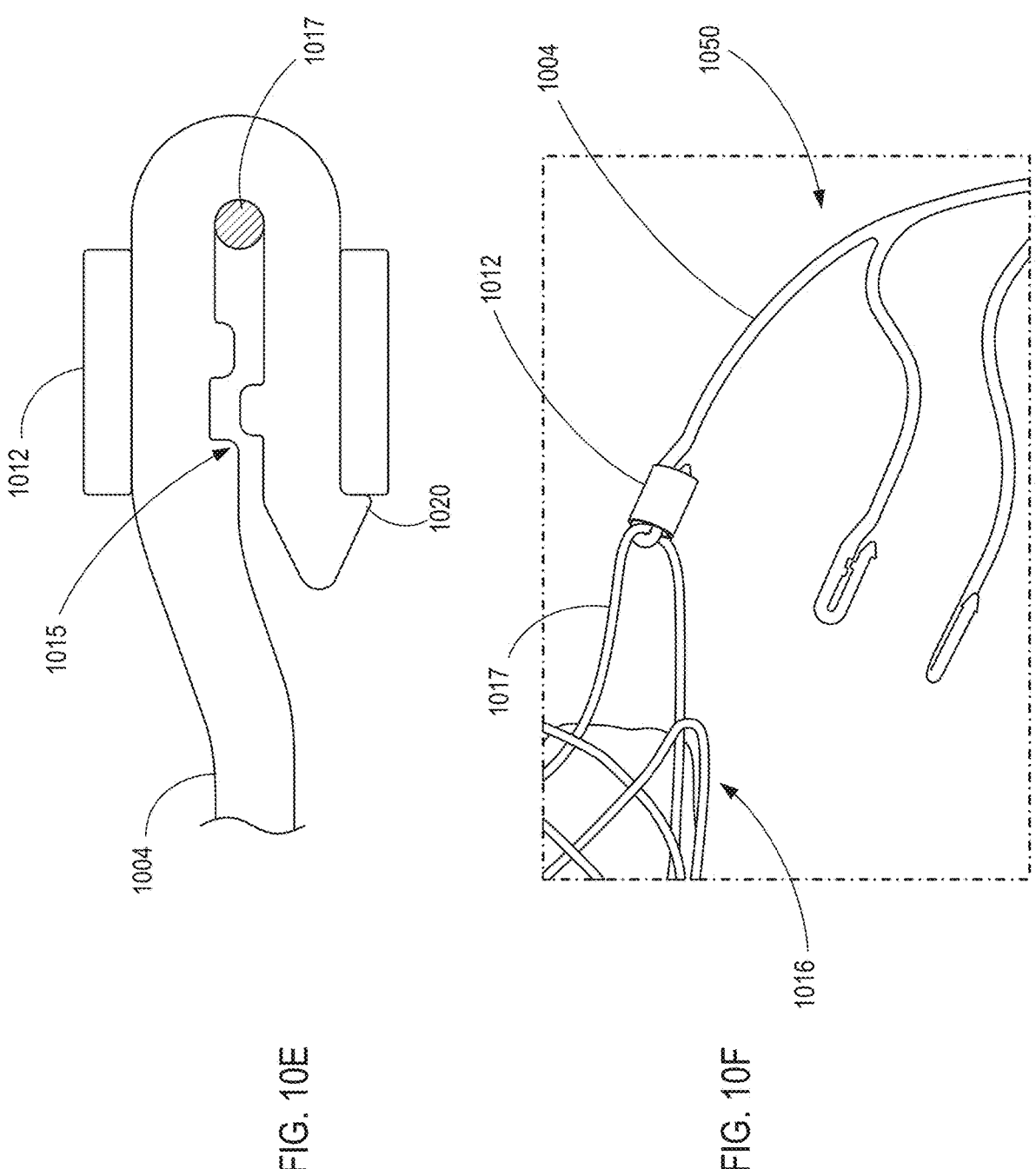

Referring now to FIG. 10E, clip 1012 is illustrated connected to strut 1004 and securing strut 1004 to loop 1017 of braided section 1016 (not shown) of the elongated tube. As shown in FIG. 10E, an end of strut 1004 may be formed into a U-shape at its proximal end. Hoop 1017 of braided section 1016 may be positioned within such U-shape. Strut 1004 may further include toothed engagement 1015 which may include one or more indentations and corresponding protrusions designed to fit within such indentations. Clip 1012 may be a tubular structure designed to be fit over the U-shaped end of strut 1004 to cause toothed engagement to secure hoop 1017 within the U-shaped end of strut 1004.

Clip 1012 may apply a compressive force (e.g., via crimping or other suitable technique) to strut 1004 to secure hoop 1017 within strut 1004. An end of strut 1004 may further include protrusion 1020, which may interface with clip 1012 to prevent clip 1012 from sliding off of or otherwise becoming dislodged from strut. It will be understood by those skilled in the art that other suitable techniques for securing hoop 1017 to strut 1004 may be used (e.g., welding).

Referring now to FIG. 10F, hoops 1017 of braided section 1016 is illustrated connected to struts 1004 of connection structure 1050 via clips 1012. As shown in FIG. 10F, hoops 1017 extend outward from braided section 1016 and are captured by the U-shaped ends of struts 1004. Clips 1012 may then be positioned over the U-shaped ends of struts while hoops 1017 are engaged with struts 1004 to secure hoops 1017 to struts 1004.

Figure 10G:
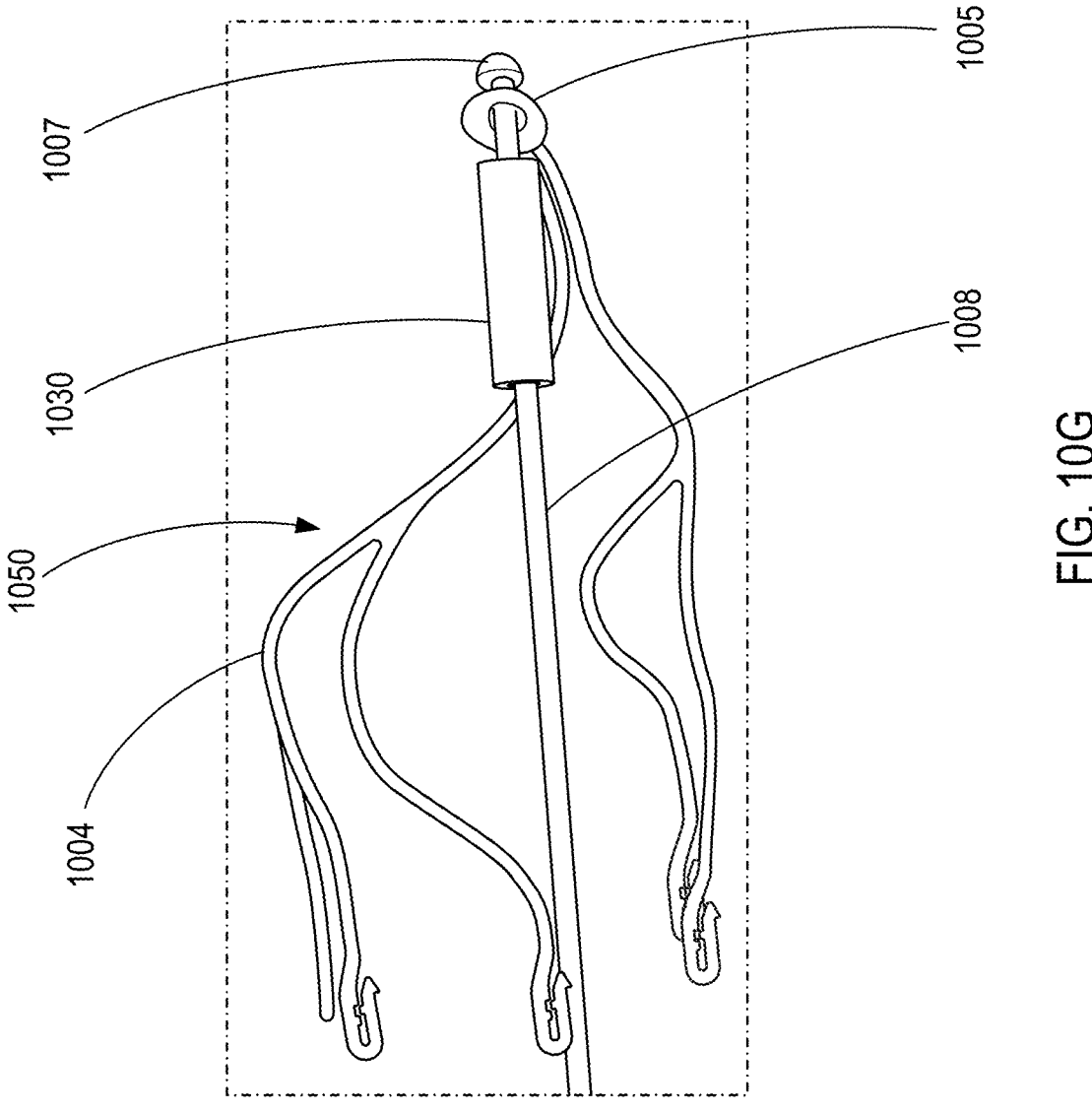

Referring now to FIG. 10G, connection structure 1050 is illustrated, which may be the same as connection structure illustrated in FIGS. 10A-10B. As shown in FIG. 10G, connection structure 1050 may include struts 1004 which may connect to hoops at the distal end of the braided section of the elongated tube. Struts may be formed together at a distal end to form disk 1005 which may include a void through which actuator wire 1008 may extend through.

Actuator wire 1008 may be connected to stopper 1007 at the distal end of actuator wire 1008 to prevent actuator wire from being removed from disk 1005. Stopper 1007 may be a ball, plate, or disk structure, or any other structure which may prevent actuation wire 1008 from exiting disk 1005. For example, stopper 1007 may be larger than the void of disk 1005. Actuation wire 1008 may be connected to tube 1030 to facilitate engagement with actuator tube 1008 and/or to maintain position of connection structure 1050 near the distal end of actuator wire 1008. Disk 1005 may be positioned between tube 1030 and ball 1070.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A catheter for introduction into a blood vessel of a patient, the catheter comprising:
   an elongated tube comprising a lumen and a distal end, the elongated tube configured to transition between an expanded state and a collapsed state, the elongated tube sized and shaped to be advanced distally through the blood vessel in the collapsed state to a target site in the blood vessel;
   an actuator tube configured to be disposed within the elongated tube;
   an actuation wire configured to be disposed within the actuator tube, the actuation wire including an elongated shaft having a distal end configured to extend distally past the distal end of the elongated tube; and
   a connection structure comprising a plurality of struts, a proximal end of each one of the plurality of struts affixed about a circumference of the distal end of the elongated tube and a distal end of each one of the plurality of struts engaged with the distal end of the actuation wire such that the distal end of the actuation wire extends distally beyond the elongated tube,
   wherein translation of the actuator tube relative to the actuation wire causes the plurality of struts to expand radially outward to transition the elongated tube to the expanded state, and
   wherein the elongated tube is coupled to a handle and the actuator tube is coupled to an actuator movably coupled to the handle and configured to move within the handle to cause the actuator tube to move.

2. The catheter of claim 1, wherein the connection structure is biased to expand radially.

3. The catheter of claim 1, wherein the actuation wire comprises a stopper at the distal end of the actuation wire.

4. The catheter of claim 3, wherein the connection structure comprises a void through which the actuation wire traverses and the stopper at the distal end of the actuation wire is larger than the void.

5. The catheter of claim 4, wherein the connection structure comprises a disk structure in which the void is posi-tioned and the distal end of each one of the plurality of struts is coupled to the disk structure.

6. The catheter of claim 4, wherein a portion of the connection structure is positioned between a distal end of the actuator tube and the stopper of the actuation wire and distal translation of the actuator tube causes the connection struc-ture to move distally to cause the elongated tube to transition to a collapsed state.

7. The catheter of claim 6, wherein proximal translation of the actuator tube permits the connection structure to move proximally thereby permitting the elongated tube to expand.

8. The catheter of claim 1, wherein the connection struc-ture comprises a plurality of radiopaque markers.

9. The catheter of claim 1, wherein a distal portion of the elongated tube comprises a braided section, wherein the braided section is configured to transition between the expanded state and the collapsed state.

10. The catheter of claim 1, wherein movement of the actuator causes the actuator tube to move with respect to the elongated tube.

11. A method for accessing a blood vessel using a catheter comprising an elongated tube, an actuator tube, and an actuation wire, the method comprising:
   advancing in a distal direction a distal end of the elon-gated tube in a collapsed state through a blood vessel to a target site within the blood vessel while the actuator tube is disposed within the elongated tube and the actuator wire is disposed within the actuator tube;
   translating the actuator tube relative to the actuation wire to cause a plurality of struts engaged with both the actuation wire and the elongated tube to expand radi-ally outward to transition the elongated tube to an expanded state within the blood vessel, wherein a distal end of the actuation wire extends distally past a distal end of the elongated tube and each one of the plurality of struts extends from the distal end of the actuation wire proximally towards the distal end of the elongated tube, each one of the plurality of struts comprising a proximal end that is affixed to a circumference of the distal end of the elongated tube and a distal end that is engaged with the distal end of the actuation wire; and
   performing an intervention within the blood vessel at the target site using the elongated tube while in the expanded state,
   wherein the plurality of struts are biased to expand radially.

12. The method of claim 11, wherein a distal portion of the elongated tube comprises a braided section, wherein the braided section is configured to transition between the expanded state and the collapsed state.

13. The method of claim 11, wherein the actuation wire comprises a stopper at the distal end of the actuation wire.

14. The method of claim 13, wherein the plurality of struts form at least a portion of a connection structure and the connection structure comprises a void through which the actuation wire traverses and wherein the stopper at the distal end of the actuation wire is larger than the void.

15. The method of claim 14, wherein the connection structure comprises a disk structure in which the void is positioned and the distal end of each one of the plurality of struts is coupled to the disk structure.

16. The method of claim 14, wherein a portion of the connection structure is positioned between a distal end of the actuator tube and the stopper.

17. The method of claim 14, wherein translating the actuator tube distally relative to the actuation wire causes the connection structure to move distally to cause the elongated tube to transition to the collapsed state.

18. The method of claim 14, wherein translating the actuator tube proximally relative to the actuation wire permits the connection structure to move proximally to permit the elongated tube to transition to the expanded state.

19. A method for accessing a blood vessel using a catheter comprising an elongated tube, an actuator tube, and an actuation wire, the method comprising:

advancing in a distal direction a distal end of the elongated tube in a collapsed state through a blood vessel to a target site within the blood vessel while the actuator tube is disposed within the elongated tube and the actuation wire is disposed within the actuator tube;

translating the actuator tube relative to the actuation wire to cause a plurality of struts engaged with both the actuation wire and the elongated tube to expand radially outward to transition the elongated tube to an expanded state within the blood vessel, wherein a distal end of the actuation wire extends distally past a distal end of the elongated tube and each one of the plurality of struts extends from the distal end of the actuation wire proximally towards the distal end of the elongated tube, each one of the plurality of struts comprising a proximal end that is affixed to a circumference of the distal end of the elongated tube and a distal end that is engaged with the distal end of the actuation wire; and performing an intervention within the blood vessel at the target site using the elongated tube while in the expanded state, wherein the elongated tube is coupled to a handle and the actuator tube is coupled to an actuator movably coupled to the handle and configured to move within the handle to cause the actuator tube to move.

20. The method of claim 19, wherein movement of the actuator causes the actuator tube to move with respect to the elongated tube.

21. A catheter for introduction into a blood vessel of a patient, the catheter comprising:

an elongated tube comprising a lumen and a distal end, the elongated tube configured to transition between an expanded state and a collapsed state, the elongated tube sized and shaped to be advanced distally through the blood vessel in the collapsed state to a target site in the blood vessel;

an actuator tube configured to be disposed within the elongated tube;

an actuation wire configured to be disposed within the actuator tube, the actuation wire including an elongated shaft having a distal end configured to extend distally past the distal end of the elongated tube; and a connection structure comprising a plurality of struts, a proximal end of each one of the plurality of struts affixed about a circumference of the distal end of the elongated tube and a distal end of each one of the plurality of struts engaged with the distal end of the actuation wire such that the distal end of the actuation wire extends distally beyond the elongated tube, wherein translation of the actuator tube relative to the actuation wire causes the plurality of struts to expand radially outward to transition the elongated tube to the expanded state, and wherein the actuation wire comprises a stopper at the distal end of the actuation wire.

22. The catheter of claim 21, wherein the connection structure comprises a void through which the actuation wire traverses and the stopper at the distal end of the actuation wire is larger than the void.

23. The catheter of claim 22, wherein the connection structure comprises a disk structure in which the void is positioned and the distal end of each one of the plurality of struts is coupled to the disk structure.

24. The catheter of claim 22, wherein a portion of the connection structure is positioned between a distal end of the actuator tube and the stopper of the actuation wire and distal translation of the actuator tube causes the connection structure to move distally to cause the elongated tube to transition to a collapsed state.

25. The catheter of claim 24, wherein proximal translation of the actuator tube permits the connection structure to move proximally thereby permitting the elongated tube to expand.

26. A catheter for introduction into a blood vessel of a patient, the catheter comprising:

an elongated tube comprising a lumen and a distal end, the elongated tube configured to transition between an expanded state and a collapsed state, the elongated tube sized and shaped to be advanced distally through the blood vessel in the collapsed state to a target site in the blood vessel;

an actuator tube configured to be disposed within the elongated tube;

an actuation wire configured to be disposed within the actuator tube, the actuation wire including an elongated shaft having a distal end configured to extend distally past the distal end of the elongated tube; and a connection structure comprising a plurality of struts, a proximal end of each one of the plurality of struts affixed about a circumference of the distal end of the elongated tube and a distal end of each one of the plurality of struts engaged with the distal end of the actuation wire such that the distal end of the actuation wire extends distally beyond the elongated tube, wherein translation of the actuator tube relative to the actuation wire causes the plurality of struts to expand radially outward to transition the elongated tube to the expanded state, and wherein the connection structure comprises a plurality of radiopaque markers.

27. A method for accessing a blood vessel using a catheter comprising an elongated tube, an actuator tube, and an actuation wire, the method comprising:

advancing in a distal direction a distal end of the elongated tube in a collapsed state through a blood vessel to a target site within the blood vessel while the actuator tube is disposed within the elongated tube and the actuator wire is disposed within the actuator tube;

translating the actuator tube relative to the actuation wire to cause a plurality of struts engaged with both the actuation wire and the elongated tube to expand radially outward to transition the elongated tube to an expanded state within the blood vessel, wherein a distal end of the actuation wire extends distally past a distal end of the elongated tube and each one of the plurality of struts extends from the distal end of the actuation wire proximally towards the distal end of the elongated tube, each one of the plurality of struts comprising a proximal end that is affixed to a circumference of the distal end of the elongated tube and a distal end that is engaged with the distal end of the actuation wire; and performing an intervention within the blood vessel at the target site using the elongated tube while in the expanded state, wherein the actuation wire comprises a stopper at the distal end of the actuation wire.

28. The method of claim 27, wherein the plurality of struts form at least a portion of a connection structure and the connection structure comprises a void through which the actuation wire traverses and wherein the stopper at the distal end of the actuation wire is larger than the void.

29. The method of claim 28, wherein the connection structure comprises a disk structure in which the void is positioned and the distal end of each one of the plurality of struts is coupled to the disk structure.

30. The method of claim 28, wherein translating the actuator tube distally relative to the actuation wire causes the connection structure to move distally to cause the elongated tube to transition to the collapsed state.

\* \* \* \* \*